United States Patent [19]

Shida et al.

[11] Patent Number: 4,820,334
[45] Date of Patent: Apr. 11, 1989

[54] 1,2,4-TRIAZOLE-3-CARBOXAMIDE COMPOUND AND A HERBICIDAL COMPOSITION CONTAINING THE SAME

[75] Inventors: Takafumi Shida; Shiro Yamazaki; Hiroyasu Shinkawa, all of Iwaki, Japan

[73] Assignee: Kureha Kagaku Kogyo Kabushiki Kaisha, Tokyo, Japan

[21] Appl. No.: 918,111

[22] Filed: Oct. 14, 1986

[30] Foreign Application Priority Data

Oct. 25, 1985 [JP] Japan .................. 60-239151
Aug. 7, 1986 [JP] Japan .................. 61-185940
Oct. 9, 1986 [JP] Japan .................. 61-239092

[51] Int. Cl.[4] .................. A01N 43/653; C07D 249/10
[52] U.S. Cl. .................. 71/92; 548/262; 548/228
[58] Field of Search .................. 71/92; 548/262

[56] References Cited

U.S. PATENT DOCUMENTS 4,327,104  4/1982  Timmler et al. .................. 548/262
4,492,597  5/1982  Aoki et al. .................. 548/262

FOREIGN PATENT DOCUMENTS 0128530  12/1984  European Pat. Off. .
2119374  11/1983  United Kingdom .................. 548/262
2120665B  12/1983  United Kingdom .

*Primary Examiner*—Richard L. Raymond
*Assistant Examiner*—Patricia L. Morris
*Attorney, Agent, or Firm*—Nixon & Vanderhye

[57] ABSTRACT

A 1,2,4-triazole-3-carboxamide compound represented by the formula (I):

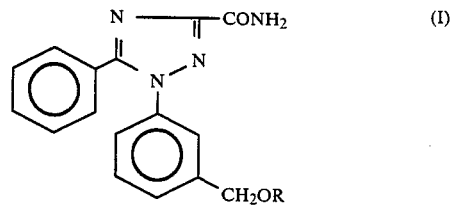

wherein R represents a straight-chain or branched-chain saturated $(C_2-C_{10})$alkyl group which is unsubstituted or substituted by fluorine atom(s); a cyclic saturated $(C_3-C_{10})$alkyl group which is unsubstituted or substituted by fluorine atom(s); a straight-chain, branched-chain or cyclic unsaturated $(C_3-C_{10})$-alkyl group which is unsubstituted or substituted by fluorine atom(s); a group represented by the formula (II):

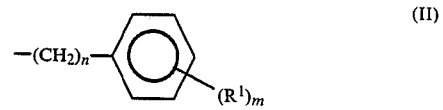

wherein $R^1$ represents a halogen atom, a $(C_1-C_3)$alkyl group, a $(C_1-C_3)$alkoxy group or a fluorine-substituted $(C_1-C_3)$alkyl group, m is an integer of from 0 to 5 and n is 0 or 1; a straight-chain or branched-chain saturated $(C_1-C_8)$alkoxy$(C_214\ C_{10})$alkyl group; a straight-chain or branched-chain unsaturated $(C_1-C_8)$alkoxy$(C_2-C_{10})$alkyl group; a phenoxy$(C_2-C_6)$alkyl group; an aralkoxy$(C_21-C_6)$alkyl group; a phenoxy$(C_2-C_6)$alkyl group having phenyl group(s) substituted by halogen atom(s) or $(C_1-C_3)$alkyl group(s); an aralkoxy$(C_2-C_6)$alkyl group having phenyl group(s) substituted by halogen atom(s) or $(C_1-C_3)$alkyl group(s); a $[(C_1-C_8)$alkoxy$(C_2-C_{10})$alkoxy]$(C_2-C_{10})$alkyl group; or a group represented by the formula (III):

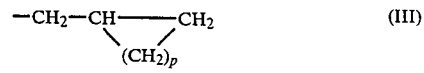

wherein p is an integer of from 1 to 8, a process for producing the same compound, and a herbicidal composition containing the 1,2,4-triazole-3-carboxamide compound as an active ingredient.

9 Claims, No Drawings

1,2,4-TRIAZOLE-3-CARBOXAMIDE COMPOUND AND A HERBICIDAL COMPOSITION CONTAINING THE SAME

BACKGROUND OF THE INVENTION

The present invention relates to a 1,2,4,-triazole-3-carboxamide compound represented by the formula (I):

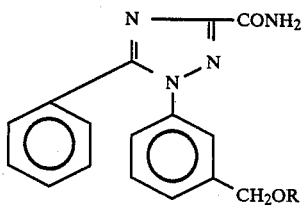

wherein R represents a straight-chain or branched-chain saturated ($C_2$–$C_{10}$)alkyl group which is unsubstituted or substituted by fluorine atom(s); a cyclic saturated ($C_3$–$C_{10}$)alkyl group which is unsubstituted or substituted by fluorine atom(s); a straight-chain, branched-chain or cyclic unsaturated ($C_3$–$C_{10}$)alkyl group which is unsubstituted or substituted by fluorine atom(s); a group represented by the formula (II):

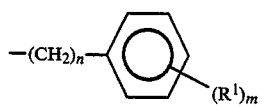

wherein $R^1$ represents a halogen atom, a ($C_1$–$C_3$)alkyl group, a ($C_1$–$C_3$)alkoxy group or a fluorine-substituted ($C_1$–$C_3$)alkyl group, m is an integer of from 0 to 5 and n is 0 or 1; a straight-chain or branched-chain saturated ($C_1$–$C_8$)alkoxy($C_2$–$C_{10}$)alkyl group; a straight-chain or branched-chain unsaturated ($C_1$–$C_8$)alkoxy($C_2$–$C_{10}$)alkyl group; a phenoxy($C_2$–$C_6$)alkyl group; an aralkoxy($C_2$–$C_6$)alkyl group; a phenoxy($C_2$–$C_6$)alkyl group having phenyl group(s) substituted by halogen atom(s) or ($C_1$–$C_3$)alkyl group(s); an aralkoxy($C_2$–$C_6$)alkyl group having phenyl group(s) substituted by halogen atom(s) or ($C_1$–$C_3$)alkyl group(s); a [($C_1$–$C_8$)alkoxy($C_2$–$C_{10}$)alkoxy]($C_2$–$C_{10}$)alkyl group; or a group represented by the formula (III):

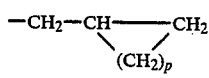

wherein p represents an integer of from 1 to 8, a process for producing the same compound and a herbicidal composition containing the 1,2,4-triazole-3-carboxamide compound as an active ingredient.

In order to protect crops such as rice, wheat, corn, etc. against noxious weeds, thereby aiming at an increased yield, it is inevitable to use herbicide (herbicidal composition).

Hitherto, as the herbicidal composition comprising a derivative of 1,5-diphenyl-1H-1,2,4-triazole-3-carboxamide as an active ingredient, for instance, a herbicidal composition comprising as an active ingredient a herbicidally effective amount of a 1,5-disubstituted 1,2,4-triazole-3-carboxamide represented by the formula:

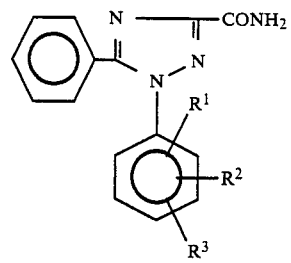

wherein $R^1$ is an alkyl group having 1 to 3 carbon atoms, a trifluoromethyl group, a chlorine atom, a fluorine atom, an iodine atom or a nitro group; $R^2$ is a methyl group, a chlorine atom or a hydrogen atom and $R^3$ is a methyl group or hydrogen atom, provided that 1-(4-methylphenyl)-5-phenyl-1,2,4-triazole-3-carboxamide is excluded, together with a herbicidally acceptable carrier or a diluent (refer to U.S. Pat. No. 4,492,597); a 1,2,4-triazole derivative represented by the formula:

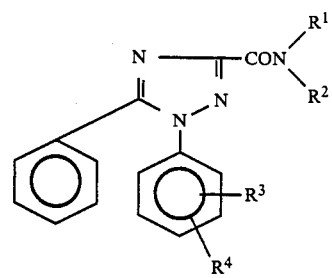

wherein $R^1$ is a hydrogen atom, an alkyl group or a hydroxyalkyl group; $R^2$ is a hydrogen atom, an alkyl group, a halogenoalkyl group, a hydroxyalkyl group, a cyanoalkyl group, an acetyl group, a halogenoacetyl group, a methoxyacetyl group, an amino group, a methoxy group or a hydroxy group and $R^3$ and $R^4$ respectively represent a hydrogen atom, an alkyl group or a halogen atom [refer to Japanese Patent Application Laying-Open (KOKAI) No. 58-194866 (1983)]; and a herbicidal composition containing a derivative of 1,2,4-triazole represented by the general formula:

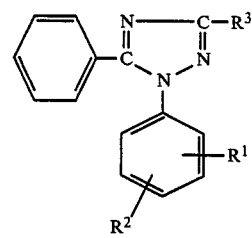

wherein $R^1$ represents a hydrogen or halogen atom or a $C_1$ or $C_2$ alkyl group; $R^2$ represents a hydrogen or halogen atom or a $C_1$ or $C_2$ alkyl, halogeno($C_1$–$C_3$)alkyl, methoxy, cyano, methoxymethyl, methylthio, methoxycarbonyl or isopropoxycarbonyl group; and $R^3$ represents a thioamide group or a group represented by the general formula:

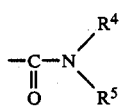

wherein $R^4$ represents a hydrogen atom or a $C_1$ or $C_2$ alkyl or hydroxy ($C_1$ or $C_2$ alkyl) group and $R^5$ represents a hydrogen atom or a $C_1$ or $C_2$ alkyl, halogeno ($C_1$ or $C_2$ alkyl), hydroxy ($C_1$ or $C_2$ alkyl), cyanomethyl, acetyl, halogenoacetyl, methoxyacetyl, amino, phenyl, methoxy, hydroxyl, $C_2$ or $C_3$ alkenyl, halogeno ($C_2$ or $C_3$ alkenyl), isopropylcarbonyl, methylthiocarbonyl or 2-methoxyethyl group (GB No. 2120665A) have been proposed.

However, the herbicidal composition containing the above-mentioned compound as an active ingredient can not be satisfied in its herbicidal activity and accordingly, an offer of a herbicide (herbicidal composition) which kills only weeds without causing any injury to crop plants even when it is applied onto crop plants and weeds at the same time, in other words, which has a high selective toxicity, has been strongly demanded.

As a result of the present inventors' studies for obtaining a compound which shows an excellent herbicidal activity and at the same time, does not cause any injury to crop plants, it has been found by the present inventors that 1,2,4-triazole-3-carboxamide represented by the formula (I) has an excellent selective herbicidal activity, and on the basis of their finding, the present inventors have completed the present invention.

The compound represented by the formula (I) is different from the known compounds as the above-mentioned herbicidal ingredient in the point that the compound represented by the formula (I) has a group —$CH_2$—O—R [R is the same as in the formula (I)].

In this connection, although the above-mentioned GB No. 2120665 A exemplifies a compound having a —$CH_2OCH_3$ group on the phenyl group of 1-position of triazole, the herbicidal activity thereof is far inferior as compared to that of the compound represented by the formula (I).

Accordingly, an object of the present invention is to provide 1,2,4-triazole-3-carboxamide represented by the formula (I) which has a selective herbicidal activity, namely, which shows an excellent herbicidal activity against gramineous plants and broad-leaved plants, particularly broad-leaved plants and on the other hand, does not show any phytotoxicity to crop plants such as rice, wheat, corn, etc. and a herbicidal composition comprising the compound represented by the formula (I) as an active ingredient as well as a process for producing the compound represented by the formula (I). cl

SUMMARY OF THE INVENTION

In a first aspect of the present invention, there is provided 1,2,4-triazole-3-carboxamide compound represented by the formula (I):

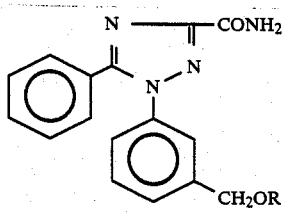

wherein R represents a straight-chain or branched-chain saturated ($C_2$–$C_{10}$)alkyl group which is unsubstituted or substituted by fluorine atom(s); a cyclic saturated ($C_3$–$C_{10}$)alkyl group which is unsubstituted or substituted by fluorine atom(s); a straight-chain, branched-chain or cyclic unsaturated ($C_3$–$C_{10}$)alkyl group which is unsubstituted or substituted by fluorine atom(s); a group represented by the formula (II):

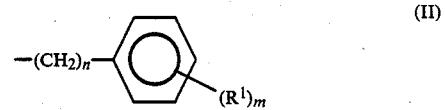

wherein $R^1$ represents a halogen atom, a ($C_1$–$C_3$)alkyl group, a ($C_1$–$C_3$)alkoxy group or a fluorine-substituted ($C_1$–$C_3$)alkyl group, m is an integer of from 0 to 5 and n is 0 or 1; a straight-chain or branched-chain saturated ($C_1$–$C_8$)alkoxy($C_2$–$C_{10}$)alkyl group; a straight-chain or branched-chain unsaturated ($C_1$–$C_8$)alkoxy($C_2$–$C_{10}$)alkyl group; a phenoxy($C_2$–$C_6$)alkyl group; an aralkoxy($C_2$–$C_6$)alkyl group; a phenoxy($C_2$–$C_6$)alkyl group having phenyl group(s) substituted by halogen atom(s) or ($C_1$–$C_3$)alkyl group(s); an aralkoxy($C_2$–$C_6$)alkyl group having phenyl group(s) substituted by halogen atom(s) or ($C_1$–$C_3$)alkyl group(s); a [($C_1$–$C_8$)alkoxy($C_2$–$C_{10}$)alkoxy]($C_2$–$C_{10}$)alkyl group; or a group represented by the formula (III):

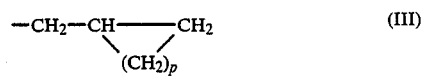

wherein p represents an integer of from 1 to 8.

In a second aspect of the present invention, there is provided a process for producing a compound 1,2,4-triazole-3-carboxamide, represented by the formula (I):

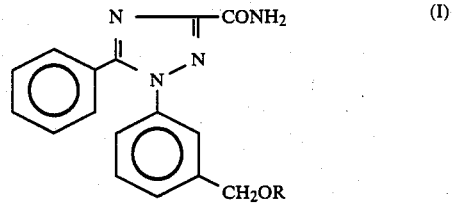

wherein R represents a straight-chain or branched-chain saturated ($C_2$–$C_{10}$)alkyl group which is unsubstituted or substituted by fluorine atom(s); a cyclic saturated ($C_3$–$C_{10}$)alkyl group which is unsubstituted or substituted by fluorine atom(s); a straight-chain, branched-chain or cyclic unsaturated ($C_3$–$C_{10}$)alkyl group which is unsubstituted or substituted by fluorine atom(s); a group represented by the formula (II):

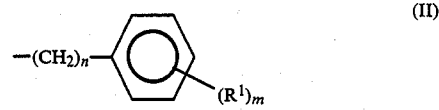

wherein $R^1$ represents a halogen atom, a ($C_1$–$C_3$)alkyl group, a ($C_1$–$C_3$)alkoxy group or a fluorine-substituted ($C_1$–$C_3$)alkyl group, m is an integer of from 0 to 5 and n is 0 or 1; a straight-chain or branched-chain saturated ($C_1$-$C_8$)alkoxy($C_2$-$C_{10}$)alkyl group; a straight-chain or branched-chain unsaturated ($C_1$-$C_8$)alkoxy($C_2$-$C_{10}$)alkyl group; a phenoxy($C_2$-$C_6$)alkyl group; an aralkoxy($C_2$-$C_6$)alkyl group; a phenoxy($C_2$-$C_6$)alkyl group having phenyl group(s) substituted by halogen atom(s) or ($C_1$-$C_3$)alkyl group(s); an aralkoxy($C_2$-$C_6$)alkyl group having phenyl group(s) substituted by halogen atom(s) or ($C_1$-$C_3$)alkyl group(s); a [($C_1$-$C_8$)alkoxy($C_2$-$C_{10}$)alkoxy]($C_2$-$C_{10}$)alkyl group; or a group represented by the formula (III):

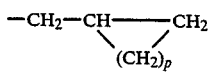
(III)

wherein p is an integer of from 1 to 8, which process comprises the steps of:

reacting a compound represented by the formula (VII):

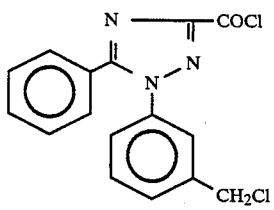
(VII)

with ammonia at a temperature in the range of from −20° C. to room temperature, thereby obtaining a compound represented by the formula (IV):

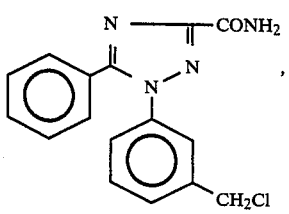
(IV)

and reacting the thus obtained compound represented by the formula (IV) with a compound represented by the formula: R—OH wherein R is the same as in the formula (I), in the presence of an inorganic- or organic base at a temperature in the range of from −20° C. to 50° C.

In a third aspect of the present invention, there is provided a process for producing a compound, 1,2,4-triazole-3-carboxamide, represented by the formula (I):

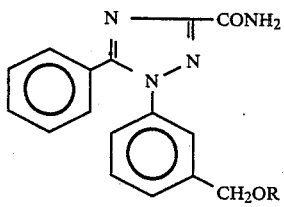
(I)

wherein R is as defined above, which process comprises the step of reacting a compound represented by the formula (VII):

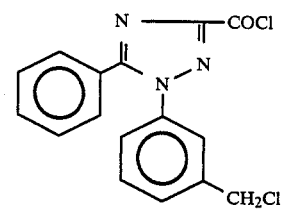
(VII)

with an amount more than one equivalent of a compound represented by the formula: R—OM wherein R is the same as in the formula (I) and M is a sodium atom or potassium atom, at a temperature in the range of from 0° to 100° C., thereby obtaining a compound represented by the formula:

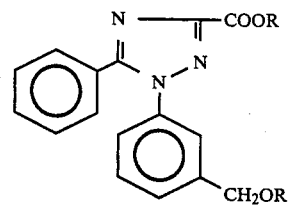

wherein R is as defined above, subjecting the thus obtained compound to hydrolysis, thereby obtaining a compound represented by the formula (VIII):

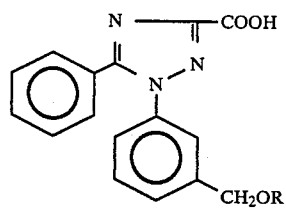
(VIII)

wherein R is as defined above,
reacting the thus obtained compound represented by the formula (VIII) with thionyl chloride at a temperature of from 60° to 100° C., thereby obtaining a compound represented by the formula:

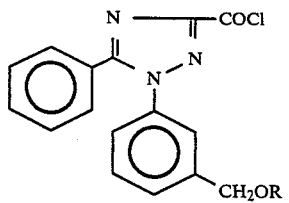

wherein R is as defined above, and
reacting the thus obtained compound with ammonia at a temperature in the range of from −20° C. to room temperature.

In a fourth aspect of the present invention, there is provided a process for producing a compound, 1,2,4-triazole-3-carboxamide represented by the formula (I):

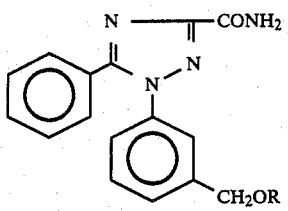

wherein R is as defined above, which process comprises the steps of:

(1) reacting 3-aminobenzyl alcohol with sodium nitrite at a temperature of not more than 15° C. in the presence of hydrochloric acid, sulfuric acid or fluoroboric acid, thereby obtaining a diazonium salt represented by the formula:

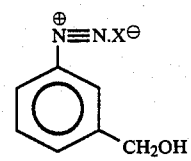

wherein X is Cl, ½ (SO$_4$) or BF$_4$, (2) reacting the thus obtained diazonium salt with 2-phenyl-2-oxazolin-5-one represented by the formula:

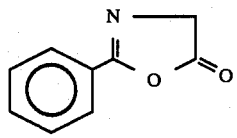

at a temperature of not more than 60° C., thereby obtaining 4-[3-(hydroxymethyl)phenylhydrazono]-2-phenyl-2-oxazolin-5-one represented by the formula (VI):

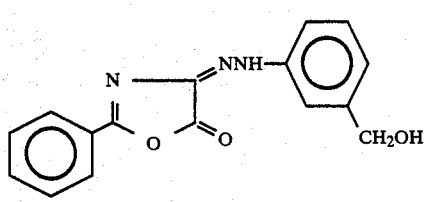

(3) after adding an amount of more than one equivalent of sodium hydroxide to the thus obtained 4-[3-(hydroxymethyl)phenylhydrazono]-2-phenyl-2-oxazolin-5-one represented by the formula (VI) in an aprotic organic solvent and reacting, adding hydrochloric acid to the thus obtained reaction mixture and heating at a temperature of not more than 100° C., thereby obtaining 1-[3-(hydroxymethyl)phenyl]-5-phenyl-1H-1,2,4-triazole-3-carboxylic acid represented by the formula (V):

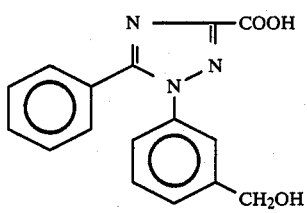

(4) reacting the thus obtained 1-[3-(hydroxymethyl)phenyl]-5-phenyl-1H-1,2,4-triazole-3-carboxylic acid represented by the formula (V) with thionyl chloride at a temperature of from 60° to 100° C., thereby obtaining a compound represented by the formula (VII):

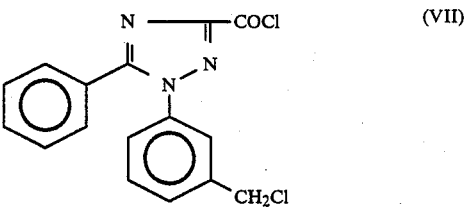

(5) reacting the thus obtained compound represented by the formula (VII) with ammonia at a temperature in the range of from −20° C. to room temperature, thereby obtaining a compound represented by the formula (IV):

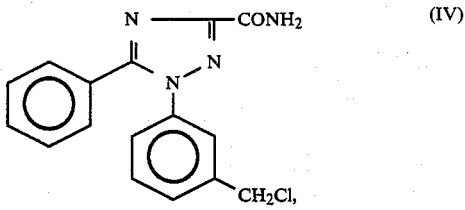

(6) reacting the thus obtained compound represented by the formula (IV) with a compound represented by the formula: R—OH wherein R is the same as in the formula (I), at a temperature in the range of from −20° to 50° C. in the presence of an inorganic base or organic base.

In a fifth aspect of the present invention, there is provided a herbicidal composition comprising a herbicidally effective amount of a 1,2,4-triazole-3-carboxamide compound represented by the formula (I):

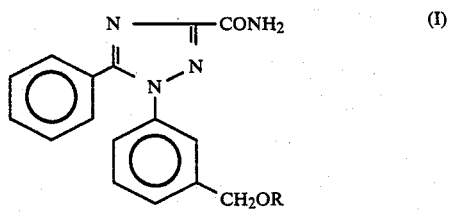

wherein R represents a straight-chain or branched-chain saturated (C$_2$–C$_{10}$)alkyl group which is unsubstituted or substituted by fluorine atom(s); a cyclic saturated (C$_3$–C$_{10}$)alkyl group which is unsubstituted or substituted by fluorine atom(s); a straight-chain, branched-chain or cyclic unsaturated (C$_3$–C$_{10}$)alkyl group which is unsubstituted or substituted by fluorine atom(s); a group represented by the formula (II):

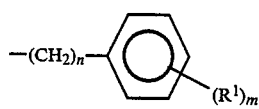

wherein $R^1$ represents a halogen atom, a $(C_1-C_3)$alkyl group, a $(C_1-C_3)$alkoxy group or a fluorine-substituted $(C_1-C_3)$alkyl group, m is an integer of from 0 to 5 and n is 0 or 1; a straight-chain or branched-chain saturated $(C_1-C_8)$alkoxy$(C_2-C_{10})$alkyl group; a straight-chain or branched-chain unsaturated $(C_1-C_8)$alkoxy$(C_2-C_{10})$alkyl group; a phenoxy$(C_2-C_6)$alkyl group; an aralkoxy$(C_2-C_6)$alkyl group; a phenoxy$(C_2-C_6)$alkyl group having phenyl group(s) substituted by halogen atom(s) or $(C_1-C_3)$alkyl group(s); an aralkoxy$(C_2-C_6)$alkyl group having phenyl group(s) substituted by halogen atom(s) or $(C_1-C_3)$alkyl group(s); a [$(C_1-C_8)$alkoxy($C_2-C_{10}$)alkoxy]$(C_2-C_{10})$alkyl group; or a group represented by the formula (III):

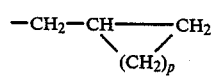

wherein p is an integer of from 1 to 8, and a herbicidally acceptable carrier or adjuvant.

In a sixth aspect of the present invention, there is provided a method for controlling the growth of noxious weeds, which method comprises applying onto noxious weeds or lands a herbicidally effective amount of 1,2,4-triazole-3-carboxamide compound represented by the formula (I):

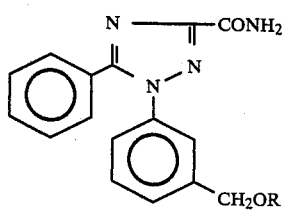

wherein R represents a straight-chain or branched-chain saturated $(C_2-C_{10})$alkyl group which is unsubstituted or substituted by fluorine atom(s); a cyclic saturated $(C_3-C_{10})$alkyl group which is unsubstituted or substituted by fluorine atom(s); a straight-chain, branched-chain or cyclic unsaturated $(C_3-C_{10})$alkyl group which is unsubstituted or substituted by fluorine atom(s); a group represented by the formula (II):

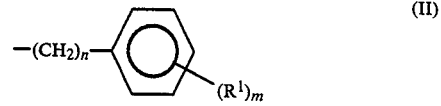

wherein $R^1$ represents a halogen atom, a $(C_1-C_3)$alkyl group, a $(C_1-C_3)$alkoxy group or a fluorine-substituted $(C_1-C_3)$alkyl group, m is an integer of from 0 to 5 and n is 0 or 1; a straight-chain or branched-chain saturated $(C_1-C_8)$alkoxy$(C_2-C_{10})$alkyl group; a straight-chain or branched-chain unsaturated $(C_1-C_8)$alkoxy$(C_2-C_{10})$alkyl group; a phenoxy$(C_2-C_6)$alkyl group; an aralkoxy$(C_2-C_6)$alkyl group; a phenoxy$(C_2-C_6)$alkyl group having phenyl group(s) substituted by halogen atom(s) or $(C_1-C_3)$alkyl group(s); an aralkoxy$(C_2-C_6)$alkyl group having phenyl group(s) substituted by halogen atom(s) or $(C_1-C_3)$alkyl group(s); a [$(C_1-C_8)$alkoxy($C_2-C_{10}$)alkoxy]$(C_2-C_{10})$alkyl group; or a group represented by the formula (III):

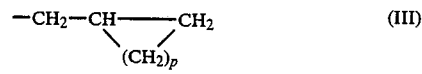

wherein p represents an integer of from 1 to 8.

DETAILED DESCRIPTION OF THE INVENTION

The 1,2,4-triazole-3-carboxamide compound has a structure represented by the formula (I), and the concrete compounds thereof and their physical properties are exemplified in Table 1.

TABLE 1

| Compound No. | R of the formula (I) | Melting point (°C.) | Nuclear Magnetic Resonance Absorption Spectrum (CDCl₃, δ, ppm) | Elementary Analysis Found / Calculated | | |
|---|---|---|---|---|---|---|
| | | | | C (%) | H (%) | N (%) |
| 1 | —CH₂CH₃ | 149–150 | 1.23(3H, t, J=7Hz), 3.56(2H, q, J=7Hz), 4.56(2H, s), 6.8(1H, bs; NH), 7.2–7.8 (10H, m; ArH + NH) | 67.18 / 67.06 | 5.52 / 5.63 | 17.17 / 17.38 |
| 2 | —CH₂CF₃ | 150–152 | 3.83(2H, q, J=7Hz), 4.75(2H, s), 6.90(1H, bs; NH), 7.4–7.6(10H, m; ArH + NH) | 57.31 / 57.44 | 4.11 / 4.02 | 14.79 / 14.89 |
| 3 | —(CH₂)₂CH₃ | 134–136 | 0.90(3H, t, J=7Hz), 1.60(2H, 6-plet, J=7Hz), 3.40(2H, t, J=6Hz), 4.53(2H, s), 6.6(1H, bs; NH), 7.1–7.8(10H, m; ArH + NH) | 67.79 / 67.84 | 5.88 / 5.99 | 16.57 / 16.66 |
| 4 | —CH₂CF₂CF₂H | 90–91 | 3.78(2H, t, t, J=13Hz,2H), 4.62(2H, s), 5.90(1H, t, t, J=54,5Hz), 6.9(1H, bs; NH), 7.1–7.7(10H, m; ArH + NH) | 55.82 / 55.88 | 3.90 / 3.95 | 13.69 / 13.72 |
| 5 | —(CH₂)₃CH₃ | 127–129 | 0.88(3H, t, J=7Hz), 1.3–1.9(4H, m), 3.40(2H, t, J=6Hz), 4.47(2H, s), 6.8(1H, bs; NH), 7.1–7.7(10H, m; ArH + NH) | 68.49 / 68.55 | 6.35 / 6.33 | 15.91 / 15.99 |
| 6 | —CH₂(CF₂)₂CF₃ | 96–97 | 3.90(2H, t, t, J=13, 3Hz), 4.67(2H, s), 6.7 (1H, bs; NH), 7.1–7.7 (10H, m; ArH + NH) | 50.40 / 50.43 | 3.18 / 3.17 | 11.59 / 11.76 |
| 7 | —(CH₂)₄CH₃ | 99–100 | 0.87(3H, t, J=7Hz), 1.1–1.7(6H, m), 3.36(2H, t, J=6Hz), 4.48(2H, s), 6.1(1H, bs; NH), 6.9–7.8(10H, m; ArH + NH) | 69.17 / 69.21 | 6.60 / 6.64 | 15.30 / 15.37 |

TABLE 1-continued

| Compound No. | R of the formula (I) | Melting point (°C.) | Nuclear Magnetic Resonance Absorption Spectrum (CDCl$_3$, δ, ppm) | Elementary Analysis Found Calculated | | |
|---|---|---|---|---|---|---|
| | | | | C (%) | H (%) | N (%) |
| 8 | —(CH$_2$)$_2$CH(CH$_3$)$_2$ | 118–120 | 0.90(6H, d, J=6Hz), 1.2–1.7(3H, m), 3.50(2H, t, J=6Hz), 4.52(2H,s), 6.9(1H, bs; NH), 7.1–7.8(10H, m; ArH + NH) | 69.18 69.21 | 6.69 6.64 | 15.38 15.37 |
| 9 | —CH$_2$C(CH$_3$)$_3$ | 147–148 | 0.85(9H, s), 3.02(2H, s), 4.47(2H, s), 6.9(1H, bs; NH), 7.1–7.7(10H, m; ArH + NH) | 69.14 69.21 | 6.60 6.64 | 15.33 15.37 |
| 10 | —(CH$_2$)$_6$CH$_3$ | Oily Matter | 0.88(3H, t, J=6Hz), 1.1–1.7(10H, m), 3.48(2H, t, J=6Hz), 4.50(2H, s), 6.8(1H, bs; NH), 6.9–7.7(10H, m) | 70.25 70.38 | 7.10 7.19 | 14.20 14.28 |
| 11 | 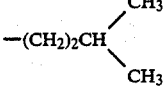 | 144–146 | 5.09(2H, s), 6.6–7.8(16H, m; ArH + NH$_2$) | 71.19 71.34 | 5.13 5.00 | 15.08 15.13 |
| 12 | 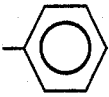 —Cl | 142–144 | 5.00(2H, s), 6.6–7.8(15H, m; ArH + NH$_2$) | 65.18 65.26 | 4.12 4.23 | 13.79 13.84 |
| 13 | 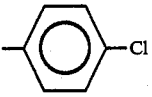 —OCH$_3$ | 139–141 | 3.70(3H, s), 4.98(2H, s), 6.5(1H, bs; NH), 6.77(4H, s; ArH), 7.1–7.7(10H, m; ArH + NH) | 68.89 69.00 | 5.01 5.03 | 13.89 13.99 |
| 14 | 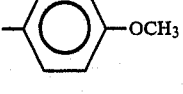 CF$_3$ | 162–163 | 5.02(2H,s ), 6.3(1H, bs; NH) 7.0–7.6(14H, m; ArH + NH) | 62.88 63.01 | 3.85 3.91 | 12.93 12.78 |
| 15 | —CH$_2$—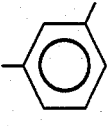 | 139–140 | 4.48(2H, s), 4.50(2H, s), 6.6(1H, bs), 7.1–7.5(15H, m; ArH + NH) | 71.72 71.86 | 5.08 5.24 | 14.63 14.58 |
| 16 | —(CH$_2$)$_2$O—(CH$_2$)$_3$CH$_3$ | Oily Matter | 0.93(3H, t, J=7Hz), 1.1–1.6(4H, m), 3.1–3.6(6H, m), 4.60(2H, s), 6.7 (1H, bs; NH), 7.1–7.6(10H, m; ArH + NH) | 67.12 66.98 | 6.72 6.64 | 14.28 14.20 |
| 17 | —(CH$_2$)$_2$O—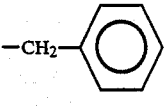 | 116–118 | 3.6–4.2(4H, m), 4.62(2H, s), 6.7–7.7(16H, m; ArH + NH$_2$) | 69.42 69.55 | 5.30 5.35 | 13.61 13.52 |
| 18 | —CH$_2$CF$_2$CF$_3$ | 115–117 | 3.86(2H, t, J=14Hz), 4.67(2H, s), 6.80(1H, bs; NH), 7.0–7.7(10H, m; ArH + NH) | 53.48 53.52 | 3.50 3.55 | 13.21 13.14 |
| 19 | —CH(CF$_3$)$_2$ | 139–140 | 4.15(1H, 7-plet, J=6Hz), 4.89(2H, s), 6.7(1H, bs; NH), 7.2–7.7 (10H, m; ArH + NH) | 51.17 51.36 | 3.23 3.18 | 12.74 12.61 |
| 20 | 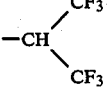 | 150–152 | 5.13(2H, s), 6.6(1H, bs; NH) 7.0–7.7(10H, m; ArH + NH) | 57.60 57.40 | 2.97 2.85 | 12.33 12.17 |
| 21 | 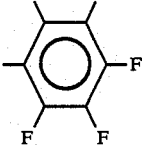 F | 156–158 | 5.10(2H, s), 6.6(1H, bs; NH), 6.8–7.8(14, m; ArH + NH) | 67.90 68.03 | 4.47 4.41 | 14.39 14.43 |

TABLE 1-continued

| Compound No. | R of the formula (I) | Melting point (°C.) | Nuclear Magnetic Resonance Absorption Spectrum (CDCl₃, δ, ppm) | Elementary Analysis Found / Calculated | | |
|---|---|---|---|---|---|---|
| | | | | C (%) | H (%) | N (%) |
| 22 | 4-F-C₆H₄- | 153–154 | 5.02(2H, s), 6.4–7.7(15H, m; ArH + NH₂) | 68.16 / 68.03 | 4.43 / 4.41 | 14.49 / 14.43 |
| 23 | 3-F-C₆H₄- | 161–162 | 5.00(2H, s), 6.6–7.7(15H, m; ArH + NH₂) | 68.24 / 68.03 | 4.49 / 4.41 | 14.38 / 14.43 |
| 24 | 2-CF₃-C₆H₄- | 190–191 | 5.17(2H, s), 6.3(1H, bs; NH), 6.6–7.8(14H, m; ArH + NH) | 62.92 / 63.01 | 3.88 / 3.91 | 12.82 / 12.78 |
| 25 | 4-CF₃-C₆H₄- | 142–144 | 5.10(2H, s), 6.6–7.8(15H, m; ArH + NH₂) | 62.88 / 63.01 | 3.87 / 3.91 | 12.76 / 12.78 |
| 26 | —CH₂—C₆H₄(4-CH₃) | 172–173 | 2.38(3H, s), 4.55(2H, s), 4.60(2H, s), 6.9(1H, bs; NH), 7.1–7.8(14H, m; ArH + NH) | 72.29 / 72.34 | 5.63 / 5.57 | 14.18 / 14.06 |
| 27 | —CH₂—C₆H₄(3-CH₃) | 104–105 | 2.34(3H, s), 4.47(2H, s), 4.53(2H, s), 6.7(1H, bs; NH), 6.9–7.7(14H, m; ArH + NH) | 72.21 / 72.34 | 5.38 / 5.57 | 14.12 / 14.06 |
| 28 | —(CH₂)₇CH₃ | Oily Matter | 0.90(3H, t, J=6Hz), 1.0–1.8(12H, m), 3.42(2H, t, J=6Hz), 4.50(2H, s), 6.8(1H, bs; NH), 7.1–7.8(10H, m; ArH + NH) | 71.08 / 70.91 | 7.52 / 7.44 | 13.86 / 13.78 |
| 29 | —(CH₂)₉CH₃ | 58–61 | 0.90(3H, t, J=6Hz), 1.0–1.8(16H, m), 3.42(2H, t, J=6Hz), 4.50(2H, s), 6.9(1H, bs; NH), 7.1–7.7(10H, m; ArH + NH) | 71.68 / 71.86 | 7.95 / 7.89 | 12.63 / 12.89 |
| 30 | —CH₂-cyclopropyl | 146–148 | 0–1.3(5H, m), 3.28(2H, d, J=7Hz), 6.9(1H, bs; NH), 7.0–7.8(10H, m; ArH + NH) | 69.03 / 68.95 | 5.82 / 5.79 | 16.13 / 16.08 |
| 31 | —(CH₂)₅CH₃ | 85–87 | 0.93(3H, t, J=6Hz), 1.0–1.9(8H, m), 3.50(2H, d, J=6Hz), 4.60(2H, s), 7.1(1H, bs; NH), 7.3–7.9(10H, m; ArH + NH) | 69.92 / 69.81 | 7.01 / 6.93 | 14.75 / 14.80 |
| 32 | —CH₂-cyclohexyl | 154–155 | 0.5–1.9(11H, m), 3.2(2H, m), 4.48(2H, s), 6.9(1H, bs; NH), 7.0–7.7(10H, m; ArH + NH) | 70.63 / 70.74 | 6.78 / 6.71 | 14.28 / 14.35 |
| 33 | —CH₂-cyclopentyl | 153–155 | 0.9–2.4(9H, m), 3.27(2H, d, J=7Hz), 4.47(2H, s), 6.9(1H, bs; NH), 6.9–7.7 (10H, m; ArH + NH) | 70.04 / 72.48 | 6.38 / 6.43 | 14.81 / 14.88 |
| 34 | —CH₂—C₆H₄(2-CH₃) | 109–111 | 2.22(3H, s), 4.42(2H, s), 4.50(2H, s), 6.7–7.6(15H, m; ArH + NH₂) | 72.48 / 72.34 | 5.66 / 5.57 | 13.88 / 14.06 |

TABLE 1-continued

| Compound No. | R of the formula (I) | Melting point (°C.) | Nuclear Magnetic Resonance Absorption Spectrum (CDCl$_3$, δ, ppm) | Elementary Analysis Found / Calculated | | |
|---|---|---|---|---|---|---|
| | | | | C (%) | H (%) | N (%) |
| 35 | —CH(CH$_3$)$_2$ 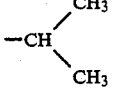 | 143–144 | 1.07(6H, d, J=6Hz), 3.60(1H, 7-plet, J=6Hz), 4.47(2H, s), 7.2–7.6(9H, m; ArH) 7.6(1H, bs; NH), 7.9(1H, bs; NH)* | 67.68 67.84 | 6.18 5.99 | 16.73 16.66 |
| 36 | —CH$_2$CH(CH$_3$)$_2$ 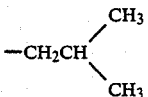 | 105–106 | 0.83(6H, d, J=6Hz), 1.80(1H, m), 3.15(2H, d; J=7Hz), 4.50(2H, s), 7.3–7.5(9H, m; ArH), 7.8(1H, bs; NH), 7.9(1H, bs; NH)* | 68.43 68.55 | 6.14 6.33 | 16.08 15.99 |
| 37 | —CH(CH$_3$)CH$_2$CH$_2$CH$_3$  | 81–83 | 0.83(3H, t, J=6Hz), 1.07(3H, d, J=6Hz), 1.1–1.8(4H, m), 3.40(1H, 6-plet, J=6Hz), 4.48(2H, s), 7.2–7.6(9H, m; ArH), 7.7(1H, bs; NH), 7.9(1H, bs; NH)* | 69.07 69.21 | 6.52 6.64 | 15.30 15.37 |
| 38 | —CH$_2$–C$_6$H$_4$–Cl (4-Cl) 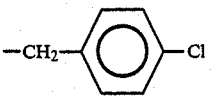 | 158–160 | 4.48(2H, s), 4.57(2H, s), 7.0–7.7(13H, m; ArH), 7.7(1H, bs; NH), 7.9(1H, bs; NH)* | 65.81 65.95 | 4.63 4.57 | 13.16 13.38 |
| 39 | —CH$_2$–C$_6$H$_4$–Cl (3-Cl) 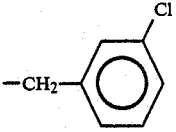 | 112–114 | 4.47(2H, s), 4.57(2H, s), 7.1–7.6(13H, m; ArH), 7.7(1H, bs; NH), 7.9(1H, bs NH)* | 66.12 65.95 | 4.39 4.57 | 13.37 13.38 |
| 40 | —CH$_2$–C$_6$H$_4$–Cl (2-Cl) 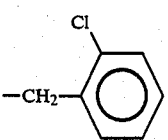 | Oily Matter | 4.55(2H, s), 4.63(2H, s), 7.2–7.7(13H, m; ArH), 7.6(1H, bs; NH), 7.9(1H, bs; NH)* | 65.87 65.95 | 4.42 4.57 | 13.19 13.38 |
| 41 | —CH$_2$–C$_6$H$_4$–F (4-F) 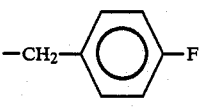 | 153–154 | 4.47(2H, s), 4.57(2H, s), 7.0–7.6(13H, m; ArH), 7.7(1H, bs; NH), 7.9(1H, bs; NH)* | 68.51 68.54 | 4.78 4.76 | 14.13 13.92 |
| 42 | —CH$_2$–C$_6$H$_4$–F (3-F) 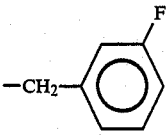 | 128–129 | 4.52(2H, s), 4.60(2H, s), 6.9–7.7(13H, m; ArH), 7.7(1H, bs; NH), 7.9(1H, bs; NH)* | 68.56 68.64 | 4.57 4.76 | 14.07 13.92 |
| 43 | —CH$_2$–C$_6$H$_4$–F (2-F) 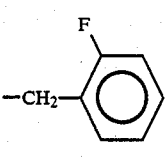 | 106–108 | 4.55(2H, s), 4.60(2H, s), 7.1–7.6(13H, m; ArH), 7.7(1H, bs; NH), 7.9(1H, bs; NH)* | 68.81 68.64 | 4.92 4.76 | 13.87 13.92 |
| 44 | 2-CH$_3$–C$_6$H$_4$– 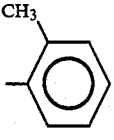 | 162–163 | 2.05(3H, s), 5.07(2H, s), 6.55–7.75(14H, m; ArH + NH), 7.8(1H, bs; NH)* | 72.01 71.86 | 5.22 5.24 | 14.41 14.58 |
| 45 | 3-CH$_3$–C$_6$H$_4$– 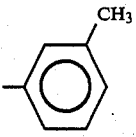 | 143–145 | 2.25(3H, s), 5.07(2H, s), 6.5–7.7(14H, m; ArH + NH), 7.9(1H, bs; NH)* | 71.94 71.86 | 5.10 5.24 | 14.39 14.58 |
| 46 | 4-CH$_3$–C$_6$H$_4$– 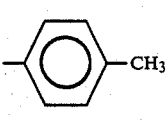 | 151–153 | 2.22(3H, s), 5.07(2H, s), 6.8–7.7(14H, m; ArH + NH), 7.9(1H, bs; NH)* | 71.90 71.86 | 5.13 5.24 | 14.80 14.58 |

TABLE 1-continued

| Compound No. | R of the formula (I) | Melting point (°C.) | Nuclear Magnetic Resonance Absorption Spectrum (CDCl₃, δ, ppm) | Elementary Analysis Found / Calculated C (%) | H (%) | N (%) |
|---|---|---|---|---|---|---|
| 47 | 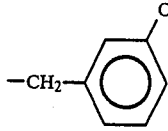 -CH₂-(C₆H₄)-OCH₃ | Resinous Matter | 3.73(3H, s), 4.43–4.57(4H, m), 6.6–7.7(15H, m; ArH + NH₂) | 69.61 / 69.55 | 5.31 / 5.35 | 13.63 / 13.52 |
| 48 | —CH₂CH₂OCH₃ | 118–119 | 3.30(3H, s), 3.53(4H, s), 4.53(2H, s), 6.9(1H, bs; NH), 7.0–7.7(10H, m; ArH + NH) | 64.91 / 64.76 | 5.88 / 5.72 | 15.82 / 15.90 |
| 49 | —CH₂CH₂OCH₂CH₃ | 65–67 | 1.20(3H, t, J=7Hz), 3.47(2H, q, J=7Hz), 3.53(4H, s), 4.55(1H, s), 6.53(1H, bs; NH) 6.9–7.7(10, m; ArH + NH) | 65.39 / 65.55 | 6.00 / 6.05 | 15.20 / 15.29 |
| 50 | —CH₂CH₂OCH(CH₃)₂ | 84–86 | 1.12(6H, d, J=7Hz), 3.5(1H, 7-plet, J=7Hz) 3.52(4H, s), 4.55(2H, s), 6.63(1H, bs; NH), 7.1–7.7(10H, m; ArH + NH) | 66.10 / 66.30 | 6.37 / 6.36 | 14.79 / 14.73 |
| 51 | —CH₂CH₂O—(CH₂)₅CH₃ | 60–62 | 0.90(3H, t, J=7Hz), 1.0–1.8(8H, m), 3.50(2H, q, J=7Hz), 3.58(4H, s), 4.58(2H, s), 6.6 (1H, bs; NH), 6.9–7.7(10H, m; ArH + NH) | 68.27 / 68.22 | 7.10 / 7.16 | 13.26 / 13.26 |
| 52 | —CH₂CHCH₂CH₃ with CH₃ | 96–98 | 0.80(3H, t, J=6Hz), 0.85(3H, d, J=6Hz), 1.0–1.9(3H, m), 3.32(2H, d, J=6Hz), 4.43(2H, s), 6.5(1H, bs; NH), 6.9–7.6(10H, m; ArH + NH) | 69.04 / 69.21 | 6.78 / 6.64 | 15.44 / 15.37 |
| 53 | —CH₂CH₂OCH₂—CH=CH₂ | 76–78 | 3.55(4H, s), 3.9–4.1(2H, m), 4.53(2H, s) 5.0–5.4(2H, m), 5.6–6.3(1H, m), 6.6(1H, bs; NH), 7.1–7.7(10H, 76-ArH + NH) | 66.61 / 66.65 | 5.69 / 5.86 | 14.80 / 14.81 |
| 54 | —CH₂CH₂OCH₂—CH(CH₃)₂ | 55–57 | 0.88(6H, d, J=6Hz), 1.88(1H, 9-plet, J=6Hz), 3.20(2H, d, J=6Hz), 3.52(4H, s), 4.58(2H, s), 6.7(1H, bs; NH), 7.0–7.7 (10H, m; ArH + NH) | 67.05 / 66.98 | 6.72 / 6.64 | 14.15 / 14.20 |
| 55 | 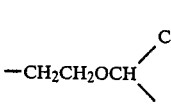 —CH₂CH₂OCH₂—C₆H₅ | Oily Matter | 3.60(4H, s), 4.53(2H, s), 4.56(2H, s), 6.6(1H, bs; NH), 7.0–7.7(15H, m; ArH + NH) | 70.21 / 70.07 | 5.72 / 5.65 | 13.04 / 13.08 |
| 56 | 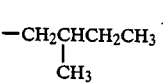 —CH₂CH₂O—(C₆H₄)-Cl | 100–102 | 3.6–3.8(2H, m), 3.9–4.1(2H, m), 4.60(2H, s), 6.4(1H, bs; NH), 6.6–7.6(14H, m; ArH + NH) | 64.33 / 64.21 | 4.85 / 4.72 | 12.31 / 12.48 |
| 57 | 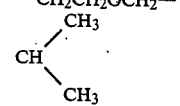 —CH₂CH₂O-(C₆H₄)-CH₃ | Oily Matter | 2.30(3H, s), 3.63–3.93(2H, m), 3.93–4.13 (2H, m), 4.60(2H, s), 6.5–7.7(15H, m; ArH + NH₂) | 70.13 / 70.07 | 5.71 / 5.65 | 13.01 / 13.08 |
| 58 | —CH₂CH₂OCH₂CH₂—O(CH₂)₃CH₃ | Oily Matter | 0.90(3H, t, J=7Hz), 1.1–1.8(4H, m), 3.50 (2H, t, J=7Hz), 3.63(8H, s), 4.57(2H, s), 6.80(1H, bs; NH), 7.1–7.7(10, m; ArH + NH) | 65.81 / 65.73 | 7.02 / 6.90 | 12.88 / 12.78 |
| 59 | —CH₂CF₂—CHFCF₃ | 94–95 | 3.5–4.1(2H, m), 4.57(2H, s), 4.90(1H, d, 6-plet, J=50,6Hz), 6.8(1H, bs; NH), 7.1–7.8(10H, m; ArH + N) | 52.29 / 52.40 | 3.48 / 3.52 | 12.32 / 12.22 |
| 60 | —CH₂(CF₂)₃CHF₂ | 105–106 | 3.87(2H, t, t, J=15,2Hz), 4.63(2H, s), 6.02(1H, t, t, J=52,6Hz), 6.6(1H, bs; NH) 7.0–7.8(10H, m; ArH + N) | 49.43 / 49.61 | 3.01 / 3.17 | 10.87 / 11.02 |
| 61 | —CH₂(CF₂)₅CHF₂ | Oily Matter | 3.89(2H, t, t, J=14,2Hz), 4.64(2H, s), 6.03(1H, t, t, J=52,6Hz), 6.7(1H, bs; NH) 7.0–7.7(10H, m; ArH + N) | 45.41 / 45.48 | 2.52 / 2.49 | 9.13 / 9.22 |
| 62 | —CH₂CH=CH₂ | 130–132 | 3.8–4.1(2H, m), 4.50(2H, s), 5.0–5.4(2H, m), 5.5–6.2(1H, m), 6.5(1H, bs; NH), 6.9–7.7(10H, m; ArH + N) | 68.41 / 68.25 | 5.28 / 5.43 | 16.62 / 16.76 |

TABLE 1-continued

| Compound No. | R of the formula (I) | Melting point (°C.) | Nuclear Magnetic Resonance Absorption Spectrum (CDCl₃, δ, ppm) | Elementary Analysis Found Calculated | | |
|---|---|---|---|---|---|---|
| | | | | C (%) | H (%) | N (%) |
| 63 | —CH₂(CF₂)₆CF₃ | 105–107 | 3.98(2H, t, t, J=14,3Hz), 4.72(2H, s), 6.6(1H, s; NH), 7.5(10H, bs; ArH + NH) | 42.50 42.61 | 2.09 2.24 | 8.19 8.28 |

*(Note)
*d₆-DMSO was used as a solvent.

The compound represented by the formula (I) can be produced by the following processes.

(1) A compound represented by the formula (VII):

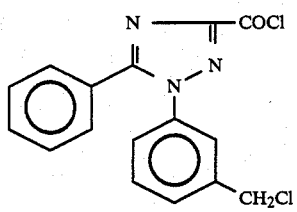

is reacted with ammonia at a temperature in the range of from −20° C. to room temperature, preferably in the range of from −10° to 5° C., thereby obtaining a novel compound, 1-[3-(chloromethyl)phenyl]-5-phenyl-1H-1,2,4-triazole-3-carboxamide, represented by the formula (IV):

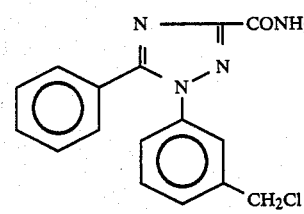

The thus obtained 1-[3-(chloromethyl)phenyl]-5-phenyl-1H-1,2,4-triazole-3-carboxamide represented by the formula (IV) is reacted with a compound represented by the formula: R—OH [wherein R is the same as in the formula (I)] in the presence of an inorganic base or an organic base, for instance, metallic sodium, sodium hydride, sodium hydroxide, potassium hydroxide, potassium carbonate or triethylamine at a temperature of from −20° to 50° C., preferably from 0° to 30° C., thereby obtaining the 1,2,4-triazole-3-carboxamide compound represented by the formula (I):

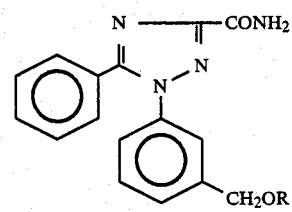

wherein R is as defined above.

Although the above-mentioned reaction can be carried out by using the alcohol derivative as a solvent, other solvent such as hexamethylphosphoric triamide, dimethylformamide, dimethylsulfoxide, acetonitrile, etc. may be used.

(2) The compound represented by the formula (VII) is reacted with an alkoxide represented by the formula: R—OM [wherein R is in the same as in the formula (I) and M is sodium atom or potassium atom] in an amount more than equivalent, preferably from 3 to 10 times of equivalent at a temperature of from 0° to 100° C., preferably from 10° to 50° C., thereby obtaining a compound represented by the formula:

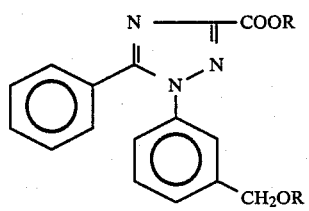

wherein R is the same as in the formula (I).

The thus obtained compound is hydrolyzed to obtain a compound represented by the formula (VIII):

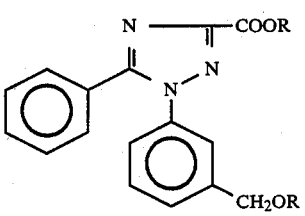

wherein R is the same as in the formula (I).

The thus obtained compound represented by the formula (VIII) is reacted with thionyl chloride at a temperature of from 60° to 100° C. to obtain a compound represented by the formula:

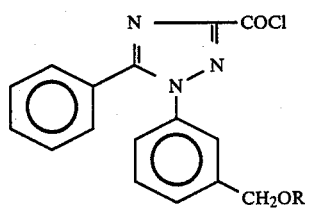

wherein R is the same as in the formula (I).

The thus obtained compound is reacted with ammonia at a temperature of from −20° C. to room temperature, preferably from −10° to 5° C., thereby obtaining the 1,2,4-triazole-3-carboxamide compound represented by the formula (I):

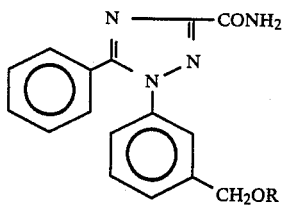

(I)

wherein R is as defined above.

The compound, 1-[3-(chloromethyl)phenyl]-5-phenyl-1H-1,2,4-triazole-3-carboxylic acid chloride, represented by the formula (VII):

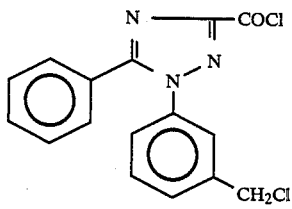

(VII)

can be produced by the following process.

Namely, a diazonium salt represented by the formula:

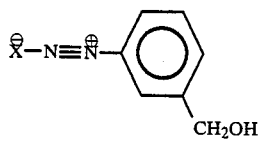

wherein X is Cl, ½ SO₄ or BF₄, obtained by reacting 3-aminobenzyl alcohol with sodium nitrite in the presence of hydrochloric acid, sulfuric acid or fluoroboric acid at a temperature of not more than 15° C., preferably from 0° to 10° C., and 2-phenyl-2-oxazolin-5-one represented by the formula:

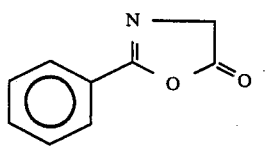

are reacted at a temperature of not more than 60° C. to obtain a novel compound, 4-[3-(hydroxymethyl)phenylhydrazono]-2-phenyl-2-oxazolin-5-one represented by the formula (VI):

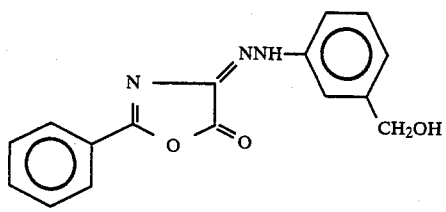

(VI)

The above-mentioned 2-phenyl-2-oxazolin-5-one is produced by subjecting hippuric acid to cyclization by dehydration.

Sodium hydroxide in an amount of more than equivalent is added to the above-mentioned 4-[3-(hydroxymethyl)phenylhydrazono]-2-phenyl-2-oxazolin-5-one in an aprotic organic solvent such as acetone, dioxane, tetrahydrofuran, dimethylformamide and methyl ethyl ketone and after reacting the mixture, hydrochloric acid is added to the mixture to adjust the pH to from 1 to 4, and then the thus adjusted mixture is heated to a temperature of lower than 100° C., preferably from 30° to 60° C., thereby obtaining a novel compound, 1-[3-(hydroxymethyl)phenyl]-5-phenyl-1H-1,2,4,-triazole-3-carboxylic acid represented by the formula (V):

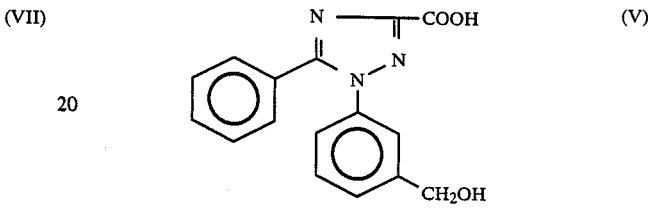

(V)

The thus obtained 1-[3-(hydroxymethyl)phenyl]-5-phenyl-1H-1,2,4-triazole-3-carboxylic acid and thionyl chloride are reacted at a temperature of from 60° to 100° C., thereby obtaining the compound, 1-[3-(chloromethyl)phenyl]-5-phenyl-1H-1,2,4-triazole-3-carboxylic acid chloride, represented by the formula (VII):

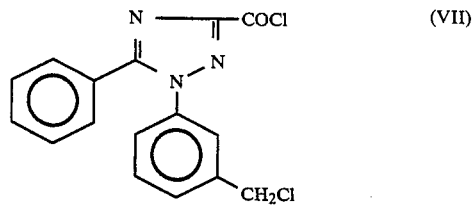

(VII)

The novel compound, 1-[3-(chloromethyl)phenyl]-5-phenyl-1H-1,2,4-triazole-3-carboxamide represented by the formula (IV):

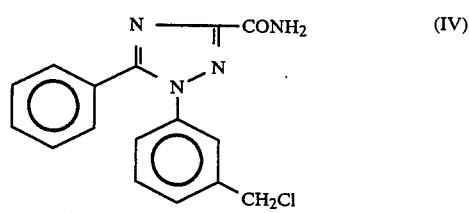

(IV)

has the following physical properties.

Melting point: 158°–160° C.

Infrared spectrum (KBr, cm$^{-1}$): $\nu_{NH}$ 3350–3150; $\nu_{CO}$ 1690 and 1660

NMR spectrum (CDCl₃, δ, ppm): 4.56 (2H, s; CH₂); 6.8–7.7 (11H, m; ArH+NH₂)

Elementary Analysis (%): (Found) C: 61.51, H: 4.21, N: 17.83; (Calculated) C: 61.44, H: 4.19, N: 17.92

The novel compound, 1-[3-(hydroxymethyl)phenyl]-5-phenyl-1H-1,2,4-triazole-3-carboxylic acid represented by the formula (V):

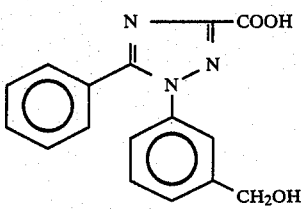

has the following physical properties.

Melting point: 192° C. (decomposed)

Infrared spectrum (KBr, cm$^{-1}$): $\nu_{OH}$, $\nu_{COOH}$ 3350, 3000–2200; 1730

NMR spectrum (d$_6$-DMSO, δ, ppm): 4.50 (2H, s; CH$_2$); Ca 6.0 (2H, bs; COOH+OH); 7.0–7.6 (9H, m; ArH)

Elementary Analysis (%): (Found) C: 65.14, H: 4.52, N: 14.10; (Calculated) C: 65.08, H: 4.44, N: 14.23

The compound, 4-[3-(hydroxymethyl)phenylhydrazono]-2-phenyl-2-oxazolin-5-one represented by the formula (VI):

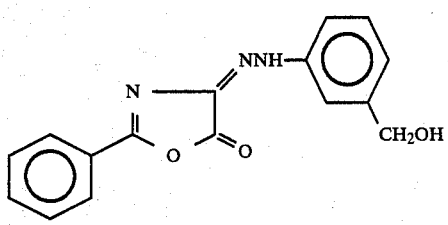

has the following physical properties.

Melting point: 172°–174° C.

Infrared spectrum (KBr, cm$^{-1}$): $\nu_{NH}$, $\nu_{OH}$: 3500–3200; $\nu_{CO}$: 1790

NMR spectrum (d$_6$-DMSO, δ, ppm): 4.51 (2H, d, J=6 Hz; CH$_2$); 5.20 (1H, , J=6 Hz; OH); 6.9–8.2 (9H, m; ArH); 12.80 (1H, s; NH)

Elementary Analysis (%): (Found) C: 64.97, H: 4.39, N: 14.20; (Calculated) C: 65.08; H: 4.44, N: 14.23

In order to utilize the 1,2,4-triazole-3-carboxamide compound obtained by each of the above-mentioned methods as an active ingredient of the herbicidal composition, the 1,2,4-triazole-3-carboxamide compound is compounded into various forms of the herbicidal composition, such as wettable powders, emulsions, granules and powders.

The herbicidal composition according to the present invention can be applied in the pre-emergence treatment and the post-emergence treatment of the paddy fields and the crop fields and the weeding treatment in orchards, flower fields and non-arable lands.

Namely, the herbicidal composition used according to the present invention comprises a herbicidally effective amount of a 1,2,4-triazole-3-carboxamide compound represented by the formula (I):

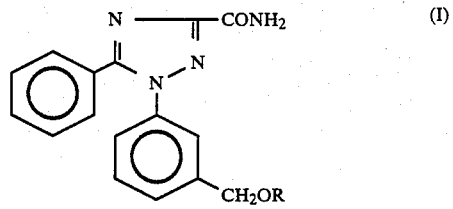

wherein R represents a straight-chain or branched-chain saturated (C$_2$–C$_{10}$)alkyl group which is unsubstituted or substituted by fluorine atom(s); a cyclic saturated (C$_3$–C$_{10}$)alkyl group which is unsubstituted or substituted by fluorine atom(s); a straight-chain, branched-chain or cyclic unsaturated (C$_3$–C$_{10}$)alkyl group which is unsubstituted or substituted by fluorine atom(s); a group represented by the formula (II):

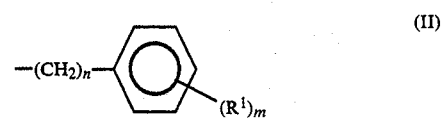

wherein R$^1$ represents a halogen atom, a (C$_1$–C$_3$)alkyl group, a (C$_1$–C$_3$)alkoxy group or a fluorine-substituted (C$_1$–C$_3$)alkyl group, m is an integer of from 0 to 5 and n is 0 or 1; a straight-chain or branched-chain saturated (C$_1$–C$_8$)alkoxy(C$_2$–C$_{10}$)alkyl group; a straight-chain or branched-chain unsaturated (C$_1$–C$_8$)alkoxy(C$_2$–C$_{10}$)alkyl group; a phenoxy(C$_2$–C$_6$)alkyl group; an aralkoxy(C$_2$–C$_6$)alkyl group; a phenoxy(C$_2$–C$_6$)alkyl group having phenyl group(s) substituted by halogen atom(s) or (C$_1$–C$_3$)alkyl group(s); an aralkoxy(C$_2$–C$_6$)alkyl group having phenyl group(s) substituted by halogen atom(s) or (C$_1$–C$_3$)alkyl group(s); a [(C$_1$–C$_8$)alkoxy(C$_2$–C$_{10}$)alkoxy](C$_2$–C$_{10}$)alkyl group; or a group represented by the formula (III):

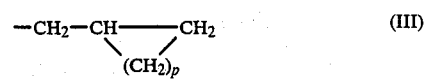

wherein p is an integer of from 1 to 8, and a herbicidally acceptable carrier or adjuvant.

As the active ingredient, 1,2,4-triazole-3-carboxamide compound in which R of the formula (I) is a straight-chain saturated (C$_2$–C$_{10}$)alkyl group; a branched-chain saturated (C$_3$–C$_7$)alkyl group; a straight-chain unsaturated (C$_3$–C$_5$)alkyl group; a straight-chain saturated (C$_2$–C$_{10}$)alkyl group which is substituted by fluorine atom(s); a branched-chain saturated (C$_3$–C$_5$)alkyl group which is substituted by fluorine atom(s); in the formula (II):

(1) a group wherein m is 0 and n is 0,
(2) a group wherein m is 1–5, R$^1$ is fluorine atom, chlorine atom, trifluoromethyl group or methoxy group and n is 0,
(3) a group wherein m is 0 and n is 1,
(4) a group wherein m is 1, R$^1$ is a fluorsine atom, chlorine atom, methyl group or methoxy group and n is 1; a straight-chain saturated (C$_1$–C$_8$)alkoxy ethyl group; a branched-chain saturated (C$_3$–C$_8$)alkoxy ethyl group; a straight-chain unsaturated (C$_3$–C$_5$)alkoxy ethyl group; phenoxy ethyl group; phenoxy ethyl group having phenyl group substituted by halogen atom or methyl group; benzyloxy ethyl group; a group of —(CH$_2$-

)$_2$—O—(CH$_2$)$_2$—O—(CH$_2$)$_3$CH$_3$; or a group wherein p is from 1 to 4 in the formula (III) is preferable from the view point of herbicidal activity and of applicable range.

Furthermore, the compound in which R to claim 2, wherein R is a straight-chain saturated (C$_2$-C$_{10}$)alkyl group; a branched-chain saturated (C$_3$-C$_5$)alkyl group; a straight-chain unsaturated (C$_3$-C$_5$)alkyl group; a straight-chain saturated (C$_2$-C$_8$)alkyl group which is substituted by fluorine atom(s); a branched-chain saturated (C$_3$-C$_5$)alkyl group which is substituted by fluorine atom(s); in the formula (II):

(1) a group wherein m is 0 and n is 0,
(2) a group wherein m is 1, R$^1$ is meta- or para-substituting fluorine atom, chlorine atom, trifluoromethyl group or methoxy group and n is 0,
(3) a group wherein m is 0 and n is 1,
(4) a group wherein m is 1, R$^1$ is a fluorine atom, chlorine atom or methyl group and n is 1; a straight-chain saturated (C$_4$-C$_5$) alkoxy ethyl group; a branched-chain saturated (C$_4$-C$_5$)alkoxy ethyl group; a group of —(CH$_2$)$_2$—O—CH$_2$CH=CH$_2$,

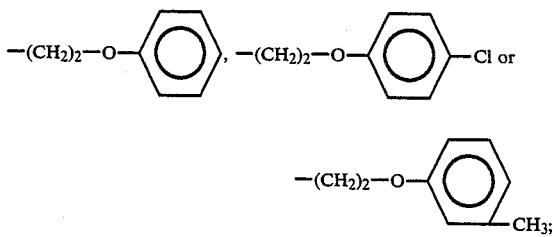

benzyloxy ethyl group; or a group wherein p is 1 to 4 in the formula (III) is more preferable from the view point of herbicidal activity and applicable range.

The present invention will be explained more in detail while referring to the following non-limitative Examples and Comparative Examples.

EXAMPLE 1

Synthesis of 1-[3-[(3-methylbutoxy)methyl]phenyl]-5-phenyl-1H-1,2,4-triazole-3-carboxamide (Compound No. 8 of Table 1)

A reaction mixture of 1-[3-(chloromethyl)phenyl]-5-phenyl-1H-1,2,4-triazole-carboxylic acid chloride obtained by adding 1.48 g (5 mM) of 1-[3-(hydroxymethyl)phenyl]-5-phenyl-1H-1,2,4-triazole-3-carboxylic acid into 5 ml of thionyl chloride and 5 ml of benzene, and refluxing the thus obtained mixture for 1.5 hours, was diluted with benzene after distilling off benzene and an excess amount of thionyl chloride. The thus diluted reaction mixture was added to a solution of an alkoxide obtained by reacting 4.4 g (50 mM) of isoamyl alcohol and 1.6 g (40 mM) of 60% NaH in 50 ml of benzene, and the thus obtained mixture was stirred for 30 min at 30° C. and then for 30 min under heating under a reflux condenser.

After adding 50 ml of water to the reaction mixture and stirring for 30 min at room temperature to hydrolyze, the thus treated mixture was separated into the aqueous layer and the organic layer to collect the aqueous layer. The organic layer was further extracted with water, and after combining the thus obtained aqueous extract with the aqueous layer, the thus combined aqueous solution was made acidic with a dilute hydrochloric acid. The thus obtained oily matter was extracted with benzene, and after dehydrating the organic layer (benzene layer), benzene was distilled off therefrom. To the thus obtained residue, 5 ml of thionyl chloride and 5 ml of benzene were added, and the thus obtained mixture was heated under a reflux condenser for 1.5 hours, and then the excess thionyl chloride was distilled off from the reaction mixture.

The thus obtained oily acid chloride was dissolved in 3 ml of dioxane, and the solution was dropped into an ice-cooled concentrated aqueous ammonia solution (20 ml). After vigorously stirring the mixture, it was neutralized with diluted hydrochloric acid, and extracted with benzene.

The thus formed organic layer was washed with water and then with an aqueous saturated saline solution, and after drying the thus washed organic layer on anhydrous sodium sulfate, benzene was distilled off therefrom.

The thus obtained crude product was purified by the silicagel chromatography (eluted by a mixture (2:1) of ethyl acetate and hexane) and recrystallized from a mixture of ethyl acetate and hexane to obtain 1.15 g of the compound (yield: 63.3%) as white crystals. The specificity of the thus obtained compound in infrared absorption spectrum is as follows:

IR(KBr, cm$^{-1}$): $\nu_{NH}$ 3470 and 3230; $\nu_{CO}$ 1710 and 1680

EXAMPLE 2

Synthesis of 1-{3-[(2,2,3,3,4,4,4,-heptafluorobutoxy)methyl]phenyl}-5-phenyl-1H-1,2,4-triazole-3-carboxamide (Compound No. 6 in Table 1)

After adding 20.65 g (0.07M) of 1-[3-(hydroxymethyl)phenyl]-5-phenyl-1H-1,2,4-triazole-3-carboxylic acid into a mixture of 80 ml (1.1M) of thionyl chloride and 80 ml of benzene and boiling the thus obtained mixture for 2 hours, benzene and the excess amount of thionyl chloride were distilled off from the reaction mixture. The thus obtained oily matter was dissolved in 30 ml of dioxane, and the solution was dropped into 300 ml of an ice-cooled concentrated aqueous ammonia solution under vigorous stirring for 30 min to obtain 1-[3-(chloromethyl)phenyl]-5-phenyl-1H-1,2,4-triazole-3-carboxamide.

313 mg (1 mM) of the thus obtained 1-[3-(chloromethyl)phenyl]-5-phenyl-1H-1,2,4-triazole-3-carboxamide was added to an alkoxide solution, which was prepared by reacting 1.4 g (7 mM) of 2,2,3,3,4,4,4-heptafluorobutanol and 0.1 g (2.5 mM) of 60% NaH in hexamethylphosphoric triamide, and the thus obtained mixture was stirred for one night. The thus obtained reaction product was made acidic with dilute hydrochloric acid and the thus obtained oily matter was extracted with benzene.

After washing the thus obtained benzene layer with water and then with an aqueous saturated saline solution, the benzene layer was dried on anhydrous sodium sulfate.

By treating the thus dried benzene layer in the same manner as in Example 1, 312 mg of the compound (yield: 65.4%) was obtained as white crystals. The specificity of the thus obtained compound in infrared absorption spectrum is as follows:

IR(KBr, cm$^{-1}$): $\nu_{NH}$ 3430, 3350 and 3240; $\nu_{CO}$ 1660.

EXAMPLE 3

Synthesis of 1-[3-(ethoxymethyl)phenyl]-5-phenyl-1H-1,2,4-triazole-3-carboxamide (Compound No. 1 of Table 1)

Into 10 ml of ethanol containing 2.5 mM of sodium ethoxide, 313 mg (1 mM) of 1-[3-(chloromethyl)-phenyl]-5-phenyl-1H-1,2,4-triazole-3-carboxamide obtained in Example 2 was added, and the thus obtained mixture was stirred for one night.

After the thus obtained reaction mixture was made acidic with dilute hydrochloric acid and ethanol was distilled off therefrom, water was added thereto and the thus obtained oily matter was extracted with benzene.

By treating the thus obtained benzene layer in the same manner as in Example 1, 205 mg of the compound (yield: 63.6%) was obtained as white crystals. The infrared absorption spectrum shows the following data:

IR(KBr, cm$^{-1}$): $\nu_{NH}$ 3400; $\nu_{CO}$ 1700.

EXAMPLE 4

Synthesis of 1-[3-(heptyloxymethyl)phenyl]-5-phenyl-1H-1,2,4-triazole-3-carboxamide (Compound No. 10 in Table 1)

A reaction mixture of 1-[3-(chloromethyl)phenyl]-5-phenyl-1H-1,2,4-triazole-3-carboxylic acid chloride obtained by adding 1.48 (5 mM) of 1-[3-(hydroxymethyl)-phenyl]-5-phenyl-1H-1,2,4-triazole-3-carboxylic acid into 5 ml of thionyl chloride and 5 ml of benzene and refluxing the thus obtaining mixture for 1.5 hours, was diluted with benzene after distilling benzene and the excess thionyl chloride. The thus diluted reaction mixture of 1-[3-(chloromethyl)phenyl]-5-phenyl-1H-1,2,4-triazole-3-carboxylic acid chloride was added to a mixture of 12 ml of heptyl alcohol and 20 ml of benzene containing 40 mM of sodium heptyloxide, and the thus formed mixture was stirred for 30 min at room temperature and then for 30 min under heating under a reflux condenser. Then, after adding 50 ml of water to the thus obtained mixture, the mixture was further stirred for 30 min at a room temperature to hydrolyze. Thereafter, the hydrolyzate was made acidic with a dilute hydrochloric acid and was diluted with hexane and then the aqueous layer was removed therefrom.

The organic layer obtained by removing the aqueous layer was washed with water and then with an aqueous saturated saline solution, and after drying the thus washed organic layer on anhydrous sodium sulfate, the solvent was distilled from the dried organic layer and the excess heptyl alcohol in the residue was removed therefrom under a reduced pressure. To the thus obtained residue, 5 ml of thionyl chloride and 5 ml of benzene were added, and after heating the thus obtained mixture under a reflux condenser for 1.5 hours, the excess thionyl chloride was distilled off therefrom.

The thus obtained oily acid chloride was dissolved in 3 ml of dioxane, and the thus obtained solution was dropped into 20 ml of a concentrated aqueous ammonia solution. After vigorously stirring the thus formed mixture for 30 min, the mixture was neutralized with dilute hydrochloric acid and the neutralizate was extracted with benzene. After washing the benzene extract with water and then with an aqueous saturated saline solution, the thus washed neutralizate was dried on anhydrous sodium sulfate and benzene was distilled off therefrom. By purifying the thus obtained crude product as the residue by the silicagel chromatography (eluted by a mixture (2:1) of ethyl acetate and hexane), 1.27 of the compound (yield: 64.9%) as a pale yellow oily substance was obtained.

Infrared absorption spectrum (liquid membrane, cm$^{-1}$) of the thus obtained compound showed the following data:

$\nu_{NH}$ 3470, 3230 and 3170; $\nu_{CO}$ 1690.

EXAMPLE 5

Synthesis of 1-{3-[(2,2,2-trifluoroethoxy)methyl]phenyl}-5-phenyl-1H-1,2,4-triazole-3-carboxamide (Compound No. 2 of Table 1)

An alkoxide was obtained by reacting 0.3 g (3 mM) of 2,2,2-trifluoroethanol and 0.1 g (2.5 mM) of 60% NaH in hexamethylphosphoric triamide. To the thus obtained alkoxide, 313 mg (1 mM) of 1-[3-(chloromethyl)-phenyl]-5-phenyl-1H-1,2,4-triazole-3-carboxamide obtained in Example 2 was added, and the thus obtained mixture was stirred for one night at room temperature. By adding dilute hydrochloric acid to thus obtained reaction mixture, thereby making acidic, the acidified reaction mixture was extracted with benzene.

After washing the benzene layer with dilute hydrochloric acid, water and an aqueous saturated saline solution, and drying the thus washed layer on anhydrous sodium sulfate, and thus dried benzene layer was treated in the same manner as in Example 1 to obtain 210 mg of the compound (yield: 55.8%) as white crystals. The infrared absorption spectrum of the thus obtained compound gave the following data:

IR(KBr, cm$^{-1}$): $\nu_{NH}$ 3480 and 3350; $\nu_{CO}$ 1680.

EXAMPLE 6

Synthesis of 1-[3-(butoxymethyl)phenyl]-5-phenyl-1H-1,2,4-triazole-3-carboxamide (Compound No. 5 of Table 1)

A reaction mixture of 1-[3-(chloromethyl)-phenyl]-5-phenyl-1H-1,2,4-triazole-3-carboxylic acid chloride obtained by adding 1.18 g (4 mM) of 1-[3-(hydroxymethyl)phenyl]-5-phenyl-1H-1,2,4-triazole-3-carboxylic acid in 5 ml of thionyl chloride and 5 ml of benzene and refluxing the thus obtained mixture for 1.5 hours, was diluted with benzene after distilling benzene and the exess thionyl chloride.

The thus diluted reaction mixture added to a solution of an alkoxide obtained by reacting 5.9 g (80 mM) of butanol and 1.6 g (40 mM) of 60% NaH in 50 ml of benzene, and the thus formed mixture was stirred for 30 min at room temperature and then for 30 min under heating under a reflux condenser. Into the thus obtained product, 50 ml of water was added and the thus obtained mixture was stirred for 30 min to hydrolyze. Thereafter, the hydrolyzate was separated into an aqueous layer and an organic layer and the aqueous layer was collected. The thus obtained organic layer was extracted with water, and the aqueous layer and the water extract were combined and was made acidic with dilute hydrochloric acid. The thus obtained oily matter was extracted with benzene and after dehydrating the benzene layer, benzene was distilled off therefrom. To the thus obtained residue, 5 ml of thionyl chloride and 5 ml of benzene were added and the thus obtained mixture was heated for 1.5 hours under a reflux condenser, and then the excess thionyl chloride was distilled therefrom.

The thus obtained oily acid chloride was dissolved in 3 ml of dioxane and the solution was dropped into an ice-cooled concentrated aqueous ammonia solution (20 ml). After vigorously stirring the thus formed mixture for 30 min, the mixture was neutralized with dilute hydrochloric acid and the neutralizate was extracted with benzene.

After washing the benzene layer with water and then with an aqueous saturated saline solution, and thus washed benzene layer was dried on anhydrous sodium sulfate and benzene was distilled off therefrom. By purifying the thus obtained crude product by silicagel-chromatography (eluted by a mixture (2:1) of ethyl acetate and hexane), 460 mg of the compound (yield: 33.0%) was obtained as white crystals.

The specificity of the title compound in infrared absorption spectrum is as follows:

IR(KBr, cm$^{-1}$): $\nu_{NH}$ 3470 and 3250; $\nu_{CO}$ 1720 and 1670.

EXAMPLE 7

Synthesis of 1-[3-(chloromethyl)phenyl]-5-phenyl-1H-1,2,4-triazole-3-carboxamide Into a mixture of 80 ml (1.1 mM) of thionyl chloride and 80 ml of benzene, 20.65 g (0.07M) of 1-[3-(hydroxymethyl)phenyl]-5-phenyl-1H-1,2,4-triazole-3-carboxylic acid were added, and the thus obtained mixture was boiled for 2 hours. After distilling benzene and the excess thionyl chloride off from the thus obtained reaction mixture, the thus obtained oily matter was dissolved in 30 ml of dioxane and the thus obtained solution was dropped into an ice-cooled concentrated aqueous ammonia solution (300 ml) under a vigorous stirring. After stirring the thus formed mixture for 30 min, the thus formed precipitate was collected by filtration, washed with water and dried to obtain 20.2 g of a white solid material (yield: 92.3%).

By recrystallizing the thus obtained white solid material from a mixture of ethyl acetate and hexane, a white crystalline substance, the compound (melting point: 158° to 160° C.) was obtained.

The infrared absorption spectrum (IR) and the nuclear magnetic resonance spectrum (NMR) of the substance are as follows:

IR(KBr, cm$^{-1}$): $\nu_{NH}$ 3350–3150; $\nu_{CO}$ 1690 and 1660
NMR (CDCl$_3$, $\delta$, ppm): 4.56 (2H, s; CH$_2$); 6.8–7.7 (11H, m; ArH+NH$_2$).

EXAMPLE 8

Synthesis of 1-[3-(hydroxymethyl)phenyl]-5-phenyl-1H-1,2,4-triazole-3-carboxylic acid Into 2 liters of acetone, 85.6 g (0.29M) of 4-[3-(hydroxymethyl)phenylhydrazono]-2-phenyl-2-oxazolin-5-one was dispersed, and the thus formed dispersion was added to an aqueous solution of 30 g (0.75M) of sodium hydroxide in 200 ml of water, and the thus formed mixture was stirred for one hour at room temperature.

After carefully adding 108 ml (1.3M) of concentrated hydrochloric acid to the thus obtained reaction mixture, the thus obtained mixture was boiled for 30 min. After distilling acetone from the reaction mixture, the crystalline residue was collected by filtration, washed well with water and dried to obtain 72.7 g of white crystals [melting point: 192° C. (decomposition)] in a yield of 84.9%.

The infrared absorption spectrum (IR) and the nuclear magnetic resonance spectrum (NMR) of the thus obtained substance are as follows:

IR(KBr, cm$^{-1}$): $\nu_{OH}$, $\nu_{COOH}$ 3350, 3000–2200, 1730
NMR(d$_6$-DMSO, $\delta$, ppm): 4.50 (2H, s; CH$_2$); Ca 6.0 (2H, bs; COOH+OH); 7.0–7.6 (9H, m; ArH).

EXAMPLE 9

Synthesis of 4-[3-(hydroxymethyl)phenylhydrazono]-2-phenyl-2-oxazolin-5-one

Into 270 ml of acetic acid anhydride, 89.5 g (0.5M) of hippuric acid was added, and the thus obtained mixture was stirred for 1.5 hours at 60° C. to obtain a uniform solution of 2-phenyl-2-oxazolin-5-one, which was preserved by cooling to −20° C.

On the other hand, into a mixed solvent of 210 ml of acetic acid and 69 ml of concentrated hydrochloric acid, 49.2 g (0.4M) of 3-aminobenzyl alcohol was dissolved, and into the thus prepared solution, a solution of 27.6 g (0.4M) of sodium nitrite in 55 ml of water was dropped at a temperature of from 0° to 5° C. to obtain a solution of diazonium salt.

After adding 63.1 g (0.77M) of anhydrous sodium acetate into the thus cooled and preserved solution of 2-phenyl-2-oxazolin-5-one, the thus obtained solution of a diazonium salt was added to the thus formed mixture at a time, and the thus obtained mixture was stirred for 4 hours at a temperature of from −20° to −15° C. and then was stirred for one hour at room temperature. Thereafter, 600 ml of water was added to the thus obtained reaction mixture and the thus formed precipitate was collected by filtration, washed with water and dried to obtain 87.9 g of orange-yellow crystals (yield: 74.5%).

By recrystallizing the thus obtained crystals from methyl ethyl ketone, the compound was obtained as orange-yellow crystals (melting point: 172° to 174° C.).

The infrared absorption spectrum (IR) and the nuclear magnetic resonance spectrum (NMR) of the thus obtained compound are as follows:

IR(KBr, cm$^{-1}$): $\nu_{NH}$, $\nu_{OH}$: 3500–3200; $\nu_{CO}$: 1790
NMR(d$_6$-DMSO, $\delta$, ppm): 4.51 (2H, d, J=6 Hz; CH$_2$); 5.20 (1H, t, J=6 Hz; OH); 6.9–8.2 (9H, m; ArH); 12.80 (1H, s; NH).

The following Examples 10 to 12 show the preparation of the herbicidal composition according to the present invention, and the following Examples 13 and 14 show the herbicidal activity thereof, the "part" in each of Examples indicating "part by weight" so far as not mentioned.

In addition, concerning Examples 13 and 14, "COMPARATIVE EXAMPLE" shown in Tables 2 and 3 indicate the herbicidal activity of the herbicidal composition containing the following compound as the active ingredient (disclosed in GB No. 2120665A).

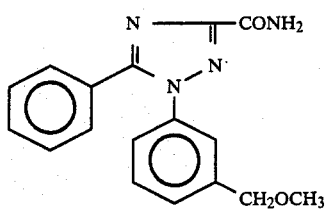

EXAMPLE 10

Preparation of a herbicidal composition of wettable powder:
50 parts of Compound No. 7 of Table 1,
5 parts of a salt of ligninsulfonic acid,
3 parts of a salt of alkylsulfonic acid and
42 parts of diatomaceous earth.

A mixture of the above-mentioned recipe was pulverized to obtain a herbicidal composition of a wettable powder form.

The herbicidal composition is applied after diluting with water.

EXAMPLE 11

Preparation of a herbicidal composition of emulsifiable concentrate:
25 parts of Compound No. 8 of Table 1,
65 parts of xylene and
10 parts of polyoxyethylene alkyl allyl ether.

The above-mentioned substances were uniformly blended to obtain a herbicidal composition of an emulsifiable concentrate form.

The herbicidal composition is applied after diluting with water.

EXAMPLE 12

Preparation of a herbicidal composition of granule form:
8 parts of Compound No. 2 of Table 1,
40 parts of bentonite,
45 parts of clay and
7 parts of ligninsulfonic acid.

The above-mentioned substances were uniformly blended and after adding water to the thus formed blend, the mixture was kneaded and extruded into granules by using an extruding pelletizer.

The thus extruded granules were dried to be the herbicidal composition of granule form.

EXAMPLE 13

Application test of the herbicidal composition on the soil before germination of plants:

Into a planter of 650 mm in length, 210 mm in width and 220 mm in depth, soil is filled in a state of crop field, and a predetermined amount of the seeds of the various test plants shown in Table 2 was sowed on the soil. After covering the thus sowed seeds with a small amount of the soil, an aqueous liquid prepared by diluting the wettable powder form of the herbicidal composition prepared in Example 10, with water so that the amount of the active ingredient (Compound No. 7) corresponds to 20 g/are of the soil surface was applied on the surface of the soil in the planter uniformly.

The thus treated planter was kept in a glass house at ordinary temperature.

After 25 days of the above-mentioned treatment, the effect of the thus applied herbicidal composition on each of the plants sowed as the seed thereof according to the following standards.

| Standards of evaluation of herbicidal effect | |
|---|---|
| Marks | Effect |
| 0 | without any herbicidal effect |
| 1 | herbicidal effect of less than 30% |
| 2 | herbicidal effect of from 31 to 50% |
| 3 | herbicidal effect of from 51 to 70% |
| 4 | herbicidal effect of from 71 to 90% |
| 5 | herbicidal effect of from 91 to 100%. |

The results of the above-mentioned application test are shown in Table 2.

TABLE 2

| Compound No. | Plants tested | | | | | | | | |
|---|---|---|---|---|---|---|---|---|---|
| | Echinochloa crus-galli | Carex iria | Setaria viridus | Bidens pilosa | Solanum nigrum | Matricaria sp. | Amaranthus retroflexus | Wheat | Corn |
| 1 | 5 | 5 | 5 | 5 | 5 | 4 | 5 | 0 | 0 |
| 2 | 5 | 5 | 5 | 5 | 5 | 5 | 5 | 0 | 1 |
| 3 | 5 | 5 | 5 | 5 | 5 | 5 | 5 | 0 | 0 |
| 4 | 5 | 5 | 5 | 5 | 5 | 5 | 5 | 0 | 1 |
| 5 | 5 | 5 | 5 | 5 | 5 | 4 | 5 | 0 | 0 |
| 6 | 5 | 5 | 5 | 5 | 5 | 5 | 5 | 0 | 1 |
| 7 | 5 | 5 | 5 | 5 | 5 | 5 | 5 | 0 | 0 |
| 8 | 5 | 5 | 5 | 5 | 5 | 4 | 5 | 0 | 0 |
| 9 | 5 | 5 | 5 | 5 | 5 | 4 | 5 | 0 | 0 |
| 10 | 5 | 5 | 5 | 5 | 5 | 4 | 5 | 0 | 0 |
| 11 | 5 | 5 | 5 | 5 | 5 | 4 | 5 | 0 | 0 |
| 12 | 5 | 5 | 5 | 5 | 5 | 4 | 5 | 0 | 0 |
| 13 | 5 | 5 | 5 | 5 | 5 | 4 | 5 | 0 | 0 |
| 14 | 5 | 5 | 5 | 5 | 5 | 4 | 5 | 0 | 0 |
| 15 | 5 | 4 | 5 | 5 | 5 | 4 | 5 | 0 | 0 |
| 16 | 5 | 5 | 5 | 5 | 5 | 4 | 5 | 0 | 0 |
| 17 | 5 | 5 | 5 | 5 | 5 | 4 | 5 | 0 | 0 |
| 18 | 5 | 5 | 5 | 5 | 5 | 5 | 5 | 0 | 1 |
| 19 | 5 | 4 | 5 | 5 | 5 | 5 | 5 | 0 | 0 |
| 20 | 5 | 4 | 5 | 5 | 5 | 5 | 5 | 0 | 0 |
| 21 | 5 | 5 | 5 | 5 | 5 | 4 | 5 | 0 | 0 |
| 22 | 5 | 5 | 5 | 5 | 5 | 5 | 5 | 0 | 0 |
| 23 | 5 | 5 | 5 | 5 | 5 | 5 | 5 | 0 | 0 |
| 24 | 3 | 4 | 3 | 4 | 4 | 4 | 4 | 0 | 0 |
| 25 | 5 | 5 | 5 | 5 | 5 | 5 | 5 | 0 | 0 |
| 26 | 5 | 5 | 5 | 5 | 5 | 5 | 5 | 0 | 0 |
| 27 | 5 | 5 | 5 | 5 | 5 | 5 | 5 | 0 | 0 |

TABLE 2-continued

| Compound No. | Echinochloa crus-galli | Carex iria | Setaria viridus | Bidens pilosa | Solanum nigrum | Matricaria sp. | Amaranthus retroflexus | Wheat | Corn |
|---|---|---|---|---|---|---|---|---|---|
| 28 | 5 | 5 | 5 | 5 | 5 | 5 | 5 | 0 | 0 |
| 29 | 5 | 5 | 5 | 5 | 5 | 5 | 5 | 0 | 0 |
| 30 | 5 | 5 | 5 | 5 | 5 | 5 | 5 | 0 | 0 |
| 31 | 5 | 5 | 5 | 5 | 5 | 5 | 5 | 0 | 0 |
| 32 | 5 | 5 | 5 | 5 | 5 | 5 | 5 | 0 | 0 |
| 33 | 5 | 5 | 5 | 5 | 5 | 5 | 5 | 0 | 0 |
| 34 | 5 | 5 | 5 | 5 | 5 | 5 | 5 | 0 | 0 |
| 35 | 5 | 5 | 5 | 5 | 5 | 5 | 5 | 0 | 0 |
| 36 | 5 | 5 | 5 | 5 | 5 | 5 | 5 | 0 | 0 |
| 37 | 5 | 5 | 5 | 5 | 5 | 5 | 5 | 0 | 0 |
| 38 | 5 | 5 | 5 | 5 | 5 | 5 | 5 | 0 | 0 |
| 39 | 5 | 5 | 5 | 5 | 5 | 5 | 5 | 0 | 0 |
| 40 | 5 | 5 | 5 | 5 | 5 | 5 | 5 | 0 | 0 |
| 41 | 5 | 5 | 5 | 5 | 5 | 5 | 5 | 0 | 0 |
| 42 | 5 | 5 | 5 | 5 | 5 | 5 | 5 | 0 | 0 |
| 43 | 5 | 5 | 5 | 5 | 5 | 5 | 5 | 0 | 0 |
| 44 | 5 | 4 | 5 | 5 | 4 | 4 | 5 | 0 | 0 |
| 45 | 5 | 4 | 5 | 5 | 5 | 5 | 5 | 0 | 0 |
| 46 | 5 | 5 | 5 | 5 | 5 | 5 | 5 | 0 | 0 |
| 47 | 5 | 5 | 5 | 5 | 5 | 5 | 5 | 0 | 0 |
| 48 | 5 | 5 | 5 | 5 | 5 | 5 | 5 | 0 | 0 |
| 49 | 5 | 5 | 5 | 5 | 5 | 5 | 5 | 0 | 0 |
| 50 | 5 | 5 | 5 | 5 | 5 | 5 | 5 | 0 | 0 |
| 51 | 5 | 5 | 5 | 5 | 5 | 5 | 5 | 0 | 0 |
| 52 | 5 | 5 | 5 | 5 | 5 | 5 | 5 | 0 | 0 |
| 53 | 5 | 5 | 5 | 5 | 5 | 5 | 5 | 0 | 0 |
| 54 | 5 | 5 | 5 | 5 | 5 | 5 | 5 | 0 | 0 |
| 55 | 5 | 5 | 5 | 5 | 5 | 5 | 5 | 0 | 0 |
| 56 | 5 | 5 | 5 | 5 | 5 | 5 | 5 | 0 | 0 |
| 57 | 5 | 5 | 5 | 5 | 5 | 5 | 5 | 0 | 0 |
| 58 | 5 | 5 | 4 | 5 | 5 | 5 | 5 | 0 | 0 |
| 59 | 5 | 5 | 5 | 5 | 5 | 5 | 5 | 0 | 1 |
| 60 | 5 | 5 | 5 | 5 | 5 | 5 | 5 | 0 | 1 |
| 61 | 5 | 5 | 5 | 5 | 5 | 5 | 5 | 0 | 1 |
| 62 | 5 | 5 | 5 | 5 | 5 | 5 | 5 | 0 | 0 |
| 63 | 5 | 5 | 4 | 5 | 5 | 5 | 5 | 0 | 0 |
| Comparative Example | 0 | 0 | 0 | 1 | 1 | 0 | 1 | 0 | 0 |

As seen in Table 2, each of the compounds according to the present invention (Compounds Nos. 1 to 63 in Table 1) showed a herbicidal effect of nearly 100% on the noxious weeds of a broad range, and on the other hand, did not show any phytotoxicity to wheat and corn.

On the contrary to the above-mentioned results, the composition comprising the compound disclosed in GB No. 2120665A scarcely showed the herbicidal activity against the noxious weeds tested herein (refer to Comparative Example in Table 2).

EXAMPLE 14

Application test of the herbicidal composition at the plant growth stage:

The seeds of the same kinds of plants as in Example 13 were sowed in the planter in the same manner as in Example 13, and when each plant attained to the first to second leaf stage, the same dilute liquid prepared by diluting the herbicidal composition of wettable powder form prepared in Example 10, with water so that the amount of Compound No. 7 corresponds to 20 g/are of the surface area of the soil in the planter as applied uniformly on the surface of the soil in the pot.

The thus treated plants were kept in a green house for 25 days and then the herbicidal effects appearing on the plants are observed and evaluated by the standards as in Example 13.

The results are shown in Table 3.

TABLE 3

| Compound No. | Echinochloa crus-galli | Carex iria | Setaria viridis | Bidens pilosa | Solanum nigrum | Matricaria sp. | Amaranthus retroflexus | Wheat | Corn |
|---|---|---|---|---|---|---|---|---|---|
| 1 | 4 | 4 | 4 | 5 | 4 | 3 | 5 | 0 | 0 |
| 2 | 5 | 5 | 5 | 5 | 5 | 3 | 5 | 0 | 2 |
| 3 | 4 | 4 | 4 | 5 | 5 | 3 | 5 | 0 | 0 |
| 4 | 5 | 5 | 5 | 5 | 5 | 3 | 5 | 0 | 2 |
| 5 | 4 | 4 | 4 | 5 | 5 | 4 | 5 | 0 | 0 |
| 6 | 5 | 5 | 5 | 5 | 5 | 5 | 5 | 0 | 0 |
| 7 | 4 | 4 | 4 | 5 | 5 | 4 | 5 | 1 | 2 |
| 8 | 4 | 4 | 4 | 5 | 5 | 3 | 5 | 0 | 0 |
| 9 | 4 | 4 | 4 | 5 | 5 | 3 | 5 | 0 | 1 |
| 10 | 4 | 4 | 4 | 5 | 5 | 3 | 5 | 0 | 0 |
| 11 | 3 | 4 | 3 | 5 | 4 | 3 | 5 | 0 | 0 |
| 12 | 3 | 4 | 4 | 5 | 4 | 3 | 5 | 0 | 0 |
| 13 | 3 | 4 | 4 | 5 | 5 | 3 | 5 | 0 | 0 |

TABLE 3-continued

| Compound No. | Echinochloa crus-galli | Carex iria | Setaria viridis | Bidens pilosa | Solanum nigrum | Matricaria sp. | Amaranthus retroflexus | Wheat | Corn |
|---|---|---|---|---|---|---|---|---|---|
| 14 | 3 | 4 | 3 | 5 | 5 | 3 | 5 | 0 | 0 |
| 15 | 3 | 3 | 4 | 5 | 4 | 3 | 5 | 0 | 0 |
| 16 | 4 | 4 | 4 | 5 | 5 | 3 | 5 | 0 | 0 |
| 17 | 4 | 4 | 4 | 5 | 5 | 3 | 5 | 0 | 0 |
| 18 | 5 | 5 | 5 | 5 | 5 | 5 | 5 | 0 | 0 |
| 19 | 4 | 4 | 5 | 5 | 5 | 3 | 5 | 0 | 0 |
| 20 | 4 | 4 | 3 | 5 | 5 | 3 | 5 | 0 | 0 |
| 21 | 4 | 4 | 3 | 5 | 4 | 3 | 4 | 0 | 0 |
| 22 | 5 | 5 | 5 | 5 | 5 | 4 | 5 | 0 | 0 |
| 23 | 4 | 5 | 5 | 5 | 5 | 5 | 5 | 0 | 0 |
| 24 | 3 | 3 | 3 | 5 | 3 | 3 | 4 | 0 | 0 |
| 25 | 5 | 4 | 5 | 5 | 5 | 4 | 5 | 0 | 0 |
| 26 | 4 | 5 | 4 | 5 | 5 | 4 | 5 | 0 | 0 |
| 27 | 5 | 5 | 5 | 5 | 5 | 5 | 5 | 0 | 0 |
| 28 | 4 | 4 | 3 | 5 | 5 | 3 | 5 | 0 | 0 |
| 29 | 5 | 5 | 5 | 5 | 5 | 5 | 5 | 0 | 0 |
| 30 | 4 | 3 | 3 | 5 | 5 | 3 | 5 | 0 | 0 |
| 31 | 5 | 5 | 5 | 5 | 5 | 5 | 5 | 0 | 0 |
| 32 | 5 | 5 | 5 | 5 | 5 | 5 | 5 | 0 | 0 |
| 33 | 4 | 4 | 3 | 5 | 5 | 3 | 5 | 0 | 0 |
| 34 | 5 | 5 | 5 | 5 | 5 | 5 | 5 | 0 | 0 |
| 35 | 4 | 4 | 3 | 5 | 5 | 3 | 5 | 0 | 0 |
| 36 | 5 | 4 | 4 | 5 | 5 | 4 | 5 | 0 | 0 |
| 37 | 5 | 5 | 4 | 5 | 5 | 5 | 5 | 0 | 0 |
| 38 | 4 | 4 | 3 | 5 | 5 | 3 | 5 | 0 | 0 |
| 39 | 5 | 5 | 5 | 5 | 5 | 5 | 5 | 0 | 0 |
| 40 | 3 | 3 | 3 | 5 | 5 | 3 | 5 | 0 | 0 |
| 41 | 5 | 4 | 4 | 5 | 5 | 3 | 5 | 0 | 0 |
| 42 | 5 | 5 | 5 | 5 | 5 | 4 | 5 | 0 | 0 |
| 43 | 5 | 5 | 5 | 5 | 5 | 5 | 5 | 0 | 0 |
| 44 | 4 | 4 | 3 | 5 | 3 | 3 | 5 | 0 | 0 |
| 45 | 3 | 4 | 3 | 5 | 4 | 3 | 5 | 0 | 0 |
| 46 | 3 | 3 | 3 | 5 | 3 | 3 | 5 | 0 | 0 |
| 47 | 5 | 5 | 5 | 5 | 5 | 5 | 5 | 0 | 0 |
| 48 | 4 | 3 | 4 | 5 | 4 | 5 | 4 | 0 | 0 |
| 49 | 4 | 3 | 3 | 5 | 4 | 5 | 4 | 0 | 0 |
| 50 | 4 | 3 | 3 | 5 | 3 | 5 | 4 | 0 | 0 |
| 51 | 5 | 4 | 4 | 5 | 4 | 5 | 5 | 0 | 0 |
| 52 | 5 | 5 | 5 | 5 | 5 | 5 | 5 | 0 | 0 |
| 53 | 4 | 4 | 4 | 5 | 4 | 4 | 4 | 0 | 0 |
| 54 | 4 | 4 | 4 | 5 | 4 | 5 | 4 | 0 | 0 |
| 55 | 4 | 3 | 4 | 5 | 4 | 4 | 4 | 0 | 0 |
| 56 | 5 | 5 | 5 | 5 | 5 | 5 | 5 | 0 | 0 |
| 57 | 5 | 5 | 5 | 5 | 5 | 5 | 5 | 0 | 0 |
| 58 | 3 | 3 | 4 | 5 | 4 | 3 | 4 | 0 | 0 |
| 59 | 5 | 5 | 5 | 5 | 5 | 5 | 5 | 0 | 2 |
| 60 | 5 | 5 | 5 | 5 | 5 | 5 | 5 | 0 | 2 |
| 61 | 5 | 5 | 5 | 5 | 5 | 5 | 5 | 0 | 2 |
| 62 | 4 | 4 | 5 | 5 | 5 | 3 | 5 | 0 | 0 |
| 63 | 5 | 5 | 4 | 5 | 5 | 5 | 5 | 0 | 0 |
| Comparative Example | 0 | 0 | 0 | 1 | 0 | 0 | 1 | 0 | 0 |

As seen in Table 3, after the initial growth of the plants, the compound according to the present invention showed a herbicidal effect of from 60 to 100% against the noxious weeds, and on the other hand, scarcely showed phytotoxicity to crop plants.

On the contrary to the above-mentioned results, the compound used as Comparative Example is inferior in herbicidal activity to the compound according to the present invention and is poor in practical use.

What is claimed is:

1. A 1,2,4-triazole-3-carboxamide compound represented by the formula (I):

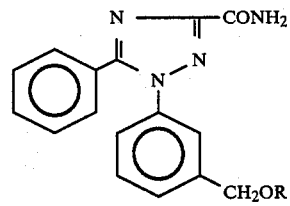

wherein R represents a straight-chain or branched-chain saturated ($C_2$–$C_{10}$)alkyl group which is unsubstituted or substituted by fluorine atom(s); a cyclic saturated ($C_3$–$C_{10}$)alkyl group which is unsubstituted or substituted by fluorine atom(s); a straight-chain, branched-chain or cyclic unsaturated ($C_3$–$C_{10}$)alkyl group which is unsubstituted or substituted by fluorine atom(s); a group represented by the formula (II):

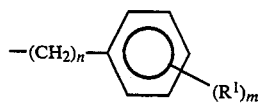 (II)

wherein $R^1$ represents a halogen atom, a ($C_1$-$C_3$)alkyl group, a ($C_1$-$C_3$)alkoxy group or a fluorine-substituted ($C_1$-$C_3$)alkyl group, m is an integer of from 0 to 5 and n is 0 or 1; a straight-chain or branched-chain saturated ($C_1$-$C_8$)alkoxy($C_2$-$C_{10}$)alkyl group; a straight-chain or branched-chain unsaturated ($C_1$-$C_8$)alkoxy($C_2$-$C_{10}$)alkyl group; a phenoxy($C_2$-$C_6$)alkyl group; an aralkoxy($C_2$-$C_6$)alkyl group; a phenoxy($C_2$-$C_6$)alkyl group having phenyl group(s) substituted by halogen atom(s) or ($C_1$-$C_3$)alkyl group(s); an aralkoxy($C_2$-$C_6$)alkyl group having phenyl group(s) substituted by halogen atom(s) or ($C_1$-$C_3$)alkyl group(s); a [($C_1$-$C_8$)alkoxy($C_2$-$C_{10}$)alkoxy]($C_2$-$C_{10}$)alkyl group; or a group represented by the formula (III):

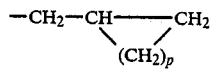 (III)

wherein p is an integer of from 1 to 8.

2. A 1,2,4-triazole-3-carboxamide compound according to claim 1, wherein R is a straight-chain saturated ($C_2$-$C_{10}$)alkyl group; a branched-chain saturated ($C_3$-$C_7$)alkyl group; a straight-chain unsaturated ($C_3$-$C_5$)alkyl group; a straight-chain saturated ($C_2$-$C_{10}$)alkyl group which is substituted by fluorine atom(s); a branched-chain saturated ($C_3$-$C_5$)alkyl group which is substituted by fluorine atom(s); in the formula (II):

(1) a group wherein m is 0 and n is 0,
(2) a group wherein m is 1-5, $R^1$ is fluorine atom, chlrine atom, trifluoromethyl group or methoxy group and n is 0,
(3) a group wherein m is 0 and n is 1,
(4) a group wherein m is 1, $R^1$ is a fluorine atom, chlorine atom, methyl group or methoxy group and n is 1; a straight-chain saturated ($C_1$-$C_8$)alkoxy ethyl group; a branched-chain saturated ($C_3$-$C_8$)alkoxy ethyl group; a straight-chain unsaturated ($C_3$-$C_5$)alkoxy ethyl group; phenoxy ethyl group; phenoxy ethyl group having phenyl group substituted by halogen atom or methyl group; benzyloxy ethyl group; a group of —($CH_2$)$_2$—O—($CH_2$)$_2$—O—($CH_2$)$_3CH_3$; or a group wherein p is from 1 to 4 in the formula (III).

3. A 1,2,4-triazole-3-carboxamide compound according to claim 2, wherein R is a straight-chain saturated ($C_2$-$C_{10}$)alkyl group; a branched-chain saturated ($C_3$-$C_5$)alkyl group; a straight-chain unsaturated ($C_3$-$C_5$)alkyl group; a straight-chain saturated ($C_2$-$C_8$)alkyl group which is substituted by fluorine atom(s); a branched-chain saturated ($C_3$-$C_5$)alkyl group which is substituted by fluorine atom(s); in the formula (II):

(1) a group wherein m is 0 and n is 0,
(2) a group wherein m is 1, $R^1$ is meta- or para-substituting fluorine atom, chlorine atom, trifluoromethyl group or methoxy group and n is 0,
(3) a group wherein m is 0 and n is 1,
(4) a group wherein m is 1, $R^1$ is a fluorine atom, chlorine atom or methyl group and n is 1; a straight-chain saturated ($C_4$-$C_5$)alkoxy ethyl group; a branched-chain saturated ($C_4$-$C_5$)alkoxy ethyl group; a group of —($CH_2$)$_2$—O—$CH_2CH=CH_2$,

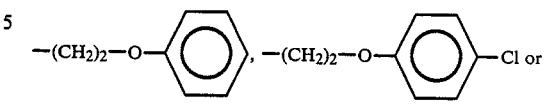

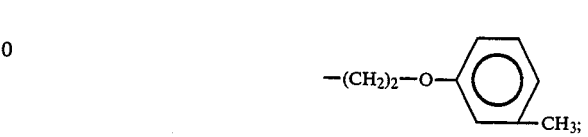

benzyloxy ethyl group; or a group wherein p is 1 to 4 in the formula (III).

4. A herbicidal composition comprising a herbicidally effective amount of a 1,2,4-triazole-3-carboxamide compound represented by the formula (I):

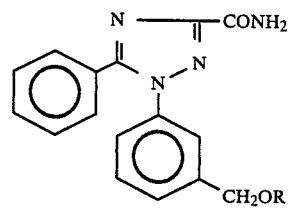 (I)

wherein R represents a straight-chain or branched-chain saturated ($C_2$-$C_{10}$)alkyl group which is unsubstituted or substituted by fluorine atom(s); a cyclic saturated ($C_3$-$C_{10}$)alkyl group which is unsubstituted or substituted by fluorine atom(s); a straight-chain, branched-chain or cyclic unsaturated ($C_3$-$C_{10}$)alkyl group which is unsubstituted or substituted by fluorine atom(s); a group represented by the formula (II):

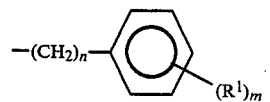 (II)

wherein $R^1$ represents a halogen atom, a ($C_1$-$C_3$)alkyl group, a ($C_1$-$C_3$)alkoxy group or a fluorine-substituted ($C_1$-$C_3$)alkyl group, m is an integer of from 0 to 5 and n is 0 or 1; a straight-chain or branched-chain saturated ($C_1$-$C_8$)alkoxy($C_2$-$C_{10}$)alkyl group; a straight-chain or branched-chain unsaturated ($C_1$-$C_8$)alkoxy($C_2$-$C_{10}$)alkyl group; a phenoxy($C_2$-$C_6$)alkyl group; an aralkoxy($C_2$-$C_6$)alkyl group; a phenoxy($C_2$-$C_6$)alkyl group having phenyl group(s) substituted by halogen atom(s) or ($C_1$-$C_3$)alkyl group(s); an aralkoxy($C_2$-$C_6$)alkyl group having phenyl group(s) substituted by halogen atom(s) or ($C_1$-$C_3$)alkyl group(s); a [($C_1$-$C_8$)alkoxy($C_2$-$C_{10}$)alkoxy]($C_2$-$C_{10}$)alkyl group; or a group represented by the formula (III):

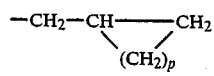 (III)

wherein p is an integer of from 1 to 8, and a herbicidally acceptable carrier or adjuvant.

5. A herbicidal composition according to claim 4, wherein R is a straight-chain saturated ($C_2$-$C_{10}$)alkyl group; a branched-chain saturated ($C_3$-$C_7$)alkyl group;

a straight-chain unsaturated (C$_3$-C$_5$)alkyl group; a straight-chain saturated (C$_2$-C$_{10}$)alkyl group which is substituted by fluorine atom(s); a branched-chain saturated (C$_3$-C$_5$)alkyl group which is substituted by fluorine atom(s); in the formula (II):
  (1) a group wherein m is 0 and n is 0,
  (2) a group wherein m is 1-5, R$^1$ is fluorine atom, chlorine atom, trifluoromethyl group or methoxy group and n is 0,
  (3) a group wherein m is 0 and n is 1,
  (4) a group wherein m is 1, R$^1$ is a fluorine atom, chlorine atom, methyl group or methoxy group and n is 1; a straight-chain saturated (C$_1$-C$_8$)alkoxy ethyl group; a branched-chain saturated (C$_3$-C$_8$)alkoxy ethyl group; a straight-chain unsaturated (C$_3$-C$_5$)alkoxy ethyl group; phenoxy ethyl group; phenoxy ethyl group having phenyl group substituted by halogen atom or methyl group; benzyloxy ethyl group; a group of —(CH$_2$)$_2$—O—(CH$_2$)$_2$—O—(CH$_2$)$_3$CH$_3$; or a group wherein p is from 1 to 4 in the formula (III).

6. A herbicidal composition according to claim 5, wherein R is a straight-chain saturated (C$_2$-C$_{10}$)alkyl group; a branched-chain saturated (C$_3$-C$_5$)alkyl group; a straight-chain unsaturated (C$_3$-C$_5$)alkyl group; a straight-chain saturated (C$_2$-C$_8$)alkyl group which is substituted by fluorine atom(s); a branched-chain saturated (C$_3$-C$_5$)alkyl group which is substituted by fluorine atom(s); in the formula (II):
  (1) a group wherein m is 0 and n is 0,
  (2) a group wherein m is 1, R$^1$ is meta- or para-substituting fluorine atom, chlorine atom, trifluoromethyl group or methoxy group and n is 0,
  (3) a group wherein m is 0 and n is 1,
  (4) a group wherein m is 1, R$^1$ is a fluorine atom, chlorine atom or methyl group and n is 1; a straight-chain saturated (C$_4$-C$_5$)alkoxy ethyl group; a branched-chain saturated (C$_4$-C$_5$)alkoxy ethyl group; a group of —(CH$_2$)$_2$—O—CH$_2$CH=CH$_2$,

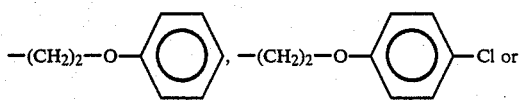, 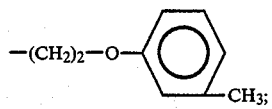

benzyloxy ethyl group; or a group wherein p is 1 to 4 in the formula (III).

7. A method for controlling the growth of noxious weeds, which method comprises applying onto noxious weeds or lands a herbicidally effective amount of 1,2,4-triazole-3-carboxamide compound represented by the formula (I):

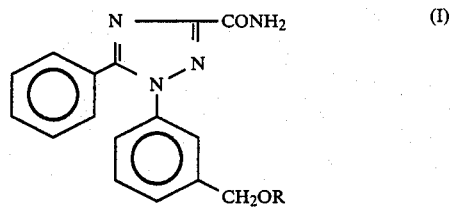

wherein R represents a straight-chain or branched-chain saturated (C$_2$-C$_{10}$)alkyl group which is unsubstituted or subtituted by fluorine atom(s); a cyclic saturated (C$_3$-C$_{10}$)alkyl group which is unsubstituted or substituted by fluorine atom(s); a straight-chain, branched-chain or cyclic unsaturated (C$_3$-C$_{10}$)alkyl group which is unsubstituted or substituted by fluorine atom(s); a group represented by the formula (II):

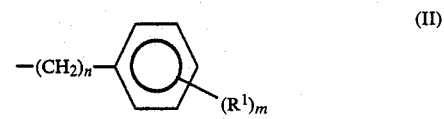

wherein R$^1$ represents a halogen atom, a (C$_1$-C$_3$)alkyl group, a (C$_1$-C$_3$)alkoxy group or a fluorine-substituted (C$_1$-C$_3$)alkyl group, m is an integer of from 0 to 5 and n is 0 or 1; a straight-chain or branched-chain saturated (C$_1$-C$_8$)alkoxy(C$_2$-C$_{10}$)alkyl group; a straight-chain or branched-chain unsaturated (C$_1$-C$_8$)alkoxy(C$_2$-C$_{10}$)alkyl group; a phenoxy(C$_2$-C$_6$)alkyl group; an aralkoxy(C$_2$-C$_6$)alkyl group; a phenoxy(C$_2$-C$_6$)alkyl group having phenyl group(s) substituted by halogen atom(s) or (C$_1$-C$_3$)alkyl group(s); an aralkoxy(C$_2$-C$_6$)alkyl group having phenyl group(s) substituted by halogen atom(s) or (C$_1$-C$_3$)alkyl group(s); a [(C$_1$-C$_8$)alkoxy(C$_2$-C$_{10}$)alkoxy](C$_2$-C$_{10}$)alkyl group; or a group represented by the formula (III):

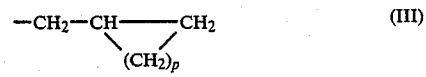

wherein p represents an integer of from 1 to 8.

8. A method according to claim 7, wherein R is a straight-chain saturated (C$_2$-C$_{10}$)alkyl group; a branched-chain saturated (C$_3$-C$_7$)alkyl group; a straight-chain unsaturated (C$_3$-C$_5$)alkyl group; a straight-chain saturated (C$_2$-C$_{10}$)alkyl group which is substituted by fluorine atom(s); a branched-chain saturated (C$_3$-C$_5$)alkyl group which is substituted by fluorine atom(s); in the formula (II):
  (1) a group wherein m is 0 and n is 0,
  (2) a group wherein m is 1-5, R$^1$ is fluorine atom, chlorine atom, trifluoromethyl group or methoxy group and n is 0,
  (3) a group wherein m is 0 and n is 1,
  (4) a group wherein m is 1, R$^1$ is a fluorine atom, chlorine atom, methyl group or methoxy group and n is 1; a straight-chain saturated (C$_1$-C$_8$)alkoxy ethyl group; a branched-chain saturated (C$_3$-C$_8$)alkoxy ethyl group; a straight-chain unsaturated (C$_3$-C$_5$)alkoxy ethyl group; phenoxy ethyl group; phenoxy ethyl group having phenyl group substituted by halogen atom or methyl group; benzyloxy ethyl group; a group of —(CH$_2$)$_2$—O—(CH$_2$ )2—O—(CH2)3CH3; or a group wherein p is from 1 to 4 in the formula (III).

9. A method according to claim 8, wherein R is a straight-chain saturated (C2-C10)alkyl group; a branched-chain saturated (C3-C5)alkyl group; a straight-chain unsaturated (C3-C5)alkyl group; a straight-chain saturated (C2-C8)alkyl group which is substituted by fluorine atom(s); a branched-chain saturated (C3-C5)alkyl group which is substituted by fluorine atom(s); in the formula (II):
(1) a group wherein m is 0 and n is 0,
(2) a group wherein m is 1, $R^1$ is meta- or para-substituting fluorine atom, chlorine atom, trifluoromethyl group or methoxy group and n is 0,
(3) a group wherein m is 0 and n is 1,
(4) a group wherein m is 1, $R^1$ is a fluorine atom, chlorine atom or methyl group and n is 1; a straight-chain saturated (C4-C5)alkoxy ethyl group; a branched-chain saturated (C4-C5)alkoxy ethyl group; a group of —(CH2)2—O—CH2CH=CH2,

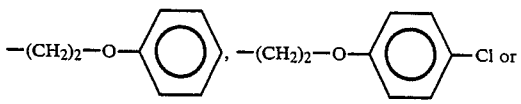, 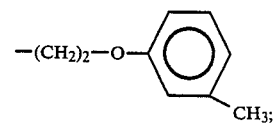

benzyloxy ethyl group; or a group wherein p is 1 to 4 in the formula (III).

* * * * *